United States Patent
Gill et al.

(10) Patent No.: US 11,259,941 B2
(45) Date of Patent: *Mar. 1, 2022

(54) PROSTHETIC FEEDBACK APPARATUS AND METHOD

(71) Applicants: Touch Bionics Limited, Livingston (GB); THE UNIVERSITY COURT OF THE UNIVERSITY OF EDINBURGH, Edinburgh (GB)

(72) Inventors: Hugh Gill, Strathclyde (GB); Sethu Vijayakumar, Lothian (GB); Ian Saunders, Yorkshire (GB)

(73) Assignee: Touch Bionics Limited, Livingston (GB)

( * ) Notice: Subject to any disclaimer, the term of this patent is extended or adjusted under 35 U.S.C. 154(b) by 205 days.

This patent is subject to a terminal disclaimer.

(21) Appl. No.: 16/550,927

(22) Filed: Aug. 26, 2019

(65) Prior Publication Data

US 2020/0054466 A1 Feb. 20, 2020

Related U.S. Application Data

(63) Continuation of application No. 14/235,282, filed as application No. PCT/GB2012/052021 on Aug. 17, 2012, now Pat. No. 10,398,576.

(30) Foreign Application Priority Data

Aug. 18, 2011 (GB) ...................................... 1114264

(51) Int. Cl.
*A61F 2/58* (2006.01)
*B25J 15/00* (2006.01)
(Continued)

(52) U.S. Cl.
CPC .............. *A61F 2/583* (2013.01); *A61F 2/588* (2013.01); *B25J 15/0009* (2013.01);
(Continued)

(58) Field of Classification Search
CPC .. A61F 2/588; A61F 2/583; A61F 2/68; A61F 2002/5058; A61F 2002/5059;
(Continued)

(56) References Cited

U.S. PATENT DOCUMENTS 1,507,682 A 9/1924 Pecorella et al.
2,445,711 A 7/1948 Fitch
(Continued)

FOREIGN PATENT DOCUMENTS

CN 1803413 7/2006
CN 106994694 8/2017
(Continued)

OTHER PUBLICATIONS

Albu-Schaffer et al., "Soft Robotics", IEEE Robotics & Automation Magazine, Sep. 2008, vol. 15, No. 3, pp. 20-30.
(Continued)

*Primary Examiner* — Christie L Bahena
(74) *Attorney, Agent, or Firm* — Knobbe, Martens, Olson & Bear, LLP (57) ABSTRACT

A prosthesis or an orthosis and method of operating the same. The prosthesis or orthosis comprising a moveable component, a motor operable to move the component, wherein the motor has at least one operating parameter, the application of which to the motor results in the component having at least one operating condition; and an electronic device operable to: determine at least one operating parameter of the motor and determine at least one instantaneous operating condition of the component from a predetermined operating profile of the motor and component and the
(Continued)

determined at least one operating parameter of the motor, the predetermined operating profile of the motor and component being based on one or more operating parameter inputs to the motor and one or more resulting operating condition outputs of the component.

20 Claims, 3 Drawing Sheets

(51) Int. Cl.
  *A61F 2/68* (2006.01)
  *A61F 2/70* (2006.01)
(52) U.S. Cl.
  CPC .......... *A61F 2002/6827* (2013.01); *A61F 2002/6836* (2013.01); *A61F 2002/701* (2013.01); *A61F 2002/704* (2013.01)
(58) Field of Classification Search
  CPC ........ A61F 2002/5061; A61F 2002/583; A61F 2002/587; A61F 2002/769; A61F 2002/6827; A61F 2002/6836; A61F 2002/701; A61F 2002/704; B25J 9/0009
  See application file for complete search history.

(56) References Cited

U.S. PATENT DOCUMENTS

| | | | |
|---|---|---|---|
| 2,477,463 A | 7/1949 | Otterman |
| 2,482,555 A | 9/1949 | Otterman |
| 2,508,156 A | 5/1950 | Gillman |
| 2,516,791 A | 7/1950 | Motis et al. |
| 2,592,842 A | 4/1952 | Alderson |
| 2,669,727 A | 2/1954 | Opuszenski |
| 2,983,162 A | 5/1961 | Musser |
| 3,406,584 A | 10/1968 | Roantree |
| 3,509,583 A | 5/1970 | Fraioli |
| 3,683,423 A | 8/1972 | Crapanzano |
| 3,751,995 A | 8/1973 | Carlson |
| 3,837,010 A | 9/1974 | Prout |
| 3,866,246 A | 2/1975 | Seamone et al. |
| 3,883,900 A | 5/1975 | Jerard et al. |
| 3,922,930 A | 12/1975 | Fletcher et al. |
| 4,030,141 A | 6/1977 | Graupe |
| 4,044,274 A | 8/1977 | Ohm |
| 4,114,464 A | 9/1978 | Schubert et al. |
| 4,197,592 A | 4/1980 | Klein |
| 4,398,110 A | 8/1983 | Flinchbaugh et al. |
| 4,558,704 A | 12/1985 | Petrofsky |
| 4,577,127 A | 3/1986 | Ferree et al. |
| 4,623,354 A | 11/1986 | Childress et al. |
| 4,678,952 A | 7/1987 | Peterson et al. |
| 4,808,187 A | 2/1989 | Patterson et al. |
| 4,813,303 A | 3/1989 | Beezer et al. |
| 4,822,238 A | 4/1989 | Kwech |
| 4,955,918 A | 9/1990 | Lee |
| 4,960,425 A | 10/1990 | Yan et al. |
| 4,990,162 A | 2/1991 | LeBlanc et al. |
| 5,020,162 A | 6/1991 | Kersten et al. |
| 5,062,673 A | 11/1991 | Mimura |
| 5,088,125 A | 2/1992 | Ansell et al. |
| 5,133,775 A | 7/1992 | Chen |
| 5,246,463 A | 9/1993 | Giampapa |
| 5,252,102 A | 10/1993 | Singer et al. |
| 5,255,188 A | 10/1993 | Telepko |
| 5,387,245 A | 2/1995 | Fay et al. |
| 5,413,454 A | 5/1995 | Movsesian |
| 5,413,611 A | 5/1995 | Haslam, II et al. |
| 5,498,472 A | 3/1996 | Gold |
| 5,501,498 A | 3/1996 | Ulrich |
| 5,581,166 A | 12/1996 | Eismann et al. |
| 5,785,960 A | 7/1998 | Rigg et al. |
| 5,851,194 A | 12/1998 | Fratrick |
| 5,852,675 A | 12/1998 | Matsuo et al. |
| 5,888,213 A | 3/1999 | Sears et al. |
| 5,888,246 A | 3/1999 | Gow |
| 5,900,714 A | 5/1999 | Dubhashi et al. |
| 6,111,973 A | 8/2000 | Holt et al. |
| 6,175,962 B1 | 1/2001 | Michelson |
| 6,223,615 B1 | 5/2001 | Huck |
| 6,244,873 B1 | 6/2001 | Hill et al. |
| 6,344,062 B1 | 2/2002 | Abboudi et al. |
| 6,361,570 B1 | 3/2002 | Gow |
| 6,494,662 B1 | 12/2002 | De Montalembert |
| 6,589,287 B2 | 7/2003 | Lundborg |
| 6,660,042 B1 | 12/2003 | Curcie et al. |
| 6,660,043 B2 | 12/2003 | Kajitani et al. |
| 6,684,754 B2 | 2/2004 | Comer |
| 6,786,112 B2 | 9/2004 | Ruttor |
| 7,056,297 B2 | 6/2006 | Dohno et al. |
| 7,144,430 B2 | 12/2006 | Archer et al. |
| 7,243,569 B2 | 7/2007 | Takahashi et al. |
| 7,316,304 B2 | 1/2008 | Heravi et al. |
| 7,316,795 B1 | 1/2008 | Knauss |
| 7,370,896 B2 | 5/2008 | Anderson et al. |
| 7,373,721 B2 | 5/2008 | Bergamasco et al. |
| 7,640,680 B1 | 1/2010 | Castro |
| 7,823,475 B2 | 11/2010 | Hirabayashi et al. |
| 7,828,857 B2 | 11/2010 | Farnsworth et al. |
| 7,867,287 B2 | 1/2011 | Puchhammer |
| 7,922,773 B1 | 4/2011 | Kuiken |
| 8,016,893 B2 | 9/2011 | Weinberg et al. |
| 8,100,986 B2 | 1/2012 | Puchhammer et al. |
| 8,197,554 B2 | 6/2012 | Whiteley et al. |
| 8,257,446 B2 | 9/2012 | Puchhammer |
| 8,337,568 B2 | 12/2012 | Macduff |
| 8,396,546 B2 | 3/2013 | Hirata et al. |
| 8,491,666 B2 | 7/2013 | Schulz |
| 8,579,991 B2 | 11/2013 | Puchhammer |
| 8,593,255 B2 | 11/2013 | Pang et al. |
| 8,657,887 B2 | 2/2014 | Gill |
| 8,662,552 B2 | 3/2014 | Torres-Jara |
| 8,663,339 B2 | 3/2014 | Inschlag et al. |
| 8,690,963 B2 | 4/2014 | Puchhammer |
| 8,696,763 B2 | 4/2014 | Gill |
| 8,808,397 B2 | 8/2014 | Gow |
| 8,821,587 B2 | 9/2014 | Lanier et al. |
| 8,828,096 B2 | 9/2014 | Gill |
| 8,840,680 B2 | 9/2014 | Goldfarb et al. |
| 8,986,395 B2 | 3/2015 | McLeary |
| 8,995,760 B2 | 3/2015 | Gill |
| 9,034,055 B2 | 5/2015 | Vinjamuri et al. |
| 9,114,030 B2 | 8/2015 | van der Merwe et al. |
| 9,121,699 B2 | 9/2015 | van der Merwe et al. |
| 9,174,339 B2 | 11/2015 | Goldfarb et al. |
| 9,265,625 B2 | 2/2016 | Goldfarb et al. |
| 9,278,012 B2 | 3/2016 | Gill |
| 9,387,095 B2 | 7/2016 | McLeary et al. |
| 9,402,749 B2 | 8/2016 | Gill et al. |
| 9,463,100 B2 | 10/2016 | Gill |
| 9,720,515 B2 | 8/2017 | Wagner et al. |
| 9,730,815 B2 | 8/2017 | Goldfarb et al. |
| 9,826,933 B2 | 11/2017 | van der Merwe et al. |
| 9,839,534 B2 | 12/2017 | Lipsey et al. |
| 9,901,465 B2 | 2/2018 | Lanier, Jr. et al. |
| 9,931,230 B2 | 4/2018 | Sikdar et al. |
| 9,999,522 B2 | 6/2018 | Gill |
| 10,265,197 B2 | 4/2019 | Gill et al. |
| 10,318,863 B2 | 8/2019 | Lock et al. |
| 10,369,016 B2 | 8/2019 | Lipsey et al. |
| 10,369,024 B2 | 8/2019 | Gill |
| 10,398,576 B2 | 9/2019 | Gill et al. |
| 10,610,385 B2 | 4/2020 | Meijer et al. |
| 2001/0023058 A1 | 9/2001 | Jung et al. |
| 2002/0016631 A1 | 2/2002 | Marchitto et al. |
| 2002/0135241 A1 | 9/2002 | Kobayashi et al. |
| 2003/0036805 A1 | 2/2003 | Senior |
| 2004/0002672 A1 | 1/2004 | Carlson |
| 2004/0078091 A1 | 4/2004 | Elkins |
| 2004/0078299 A1 | 4/2004 | Down-Logan et al. |
| 2004/0103740 A1 | 6/2004 | Townsend et al. |
| 2004/0181289 A1 | 9/2004 | Bedard et al. |
| 2004/0182125 A1 | 9/2004 | McLean |

(56) References Cited

U.S. PATENT DOCUMENTS

| | | |
|---|---|---|
| 2005/0021154 A1 | 1/2005 | Brimalm |
| 2005/0021155 A1 | 1/2005 | Brimalm |
| 2005/0093997 A1 | 5/2005 | Dalton et al. |
| 2005/0101693 A1 | 5/2005 | Arbogast et al. |
| 2005/0192677 A1 | 9/2005 | Ragnarsdottir et al. |
| 2006/0029909 A1 | 2/2006 | Kaczkowski |
| 2006/0054782 A1 | 3/2006 | Olsen et al. |
| 2006/0158146 A1 | 7/2006 | Tadano |
| 2006/0167564 A1 | 7/2006 | Flaherty et al. |
| 2006/0212129 A1 | 9/2006 | Lake et al. |
| 2006/0229755 A1 | 10/2006 | Kuiken et al. |
| 2006/0251408 A1 | 11/2006 | Konno et al. |
| 2007/0032884 A1 | 2/2007 | Veatch |
| 2007/0058860 A1 | 3/2007 | Harville et al. |
| 2007/0061111 A1 | 3/2007 | Jung et al. |
| 2007/0071314 A1 | 3/2007 | Bhatti et al. |
| 2007/0175681 A1 | 8/2007 | King et al. |
| 2007/0230832 A1 | 10/2007 | Usui et al. |
| 2007/0260328 A1 | 11/2007 | Bertels et al. |
| 2008/0058668 A1 | 3/2008 | Seyed Momen et al. |
| 2008/0146981 A1 | 6/2008 | Greenwald et al. |
| 2008/0215162 A1 | 9/2008 | Farnsworth et al. |
| 2008/0260218 A1 | 10/2008 | Smith et al. |
| 2008/0262634 A1 | 10/2008 | Puchhammer |
| 2009/0213379 A1 | 8/2009 | Carroll et al. |
| 2009/0302626 A1* | 12/2009 | Dollar ............... B25J 9/104 294/106 |
| 2010/0016990 A1 | 1/2010 | Kurtz |
| 2010/0036507 A1 | 2/2010 | Gow |
| 2010/0116078 A1 | 5/2010 | Kim |
| 2010/0274365 A1 | 10/2010 | Evans et al. |
| 2010/0328049 A1 | 12/2010 | Frysz et al. |
| 2011/0136376 A1 | 6/2011 | Johnson et al. |
| 2011/0203027 A1 | 8/2011 | Flather et al. |
| 2011/0237381 A1 | 9/2011 | Puchhammer |
| 2011/0257765 A1 | 10/2011 | Evans et al. |
| 2011/0264238 A1 | 10/2011 | van der Merwe et al. |
| 2011/0265597 A1 | 11/2011 | Long |
| 2011/0278061 A1 | 11/2011 | Farnan |
| 2012/0004884 A1 | 1/2012 | Fillol et al. |
| 2012/0014571 A1 | 1/2012 | Wong et al. |
| 2012/0061155 A1 | 3/2012 | Berger et al. |
| 2012/0099788 A1 | 4/2012 | Bhatti et al. |
| 2012/0109337 A1 | 5/2012 | Schulz |
| 2012/0123558 A1 | 5/2012 | Gill |
| 2012/0204665 A1 | 8/2012 | Baudasse |
| 2012/0280812 A1 | 11/2012 | Sheikman et al. |
| 2012/0286629 A1 | 11/2012 | Johnson et al. |
| 2012/0303136 A1 | 11/2012 | Macduff |
| 2012/0330439 A1 | 12/2012 | Goldfarb et al. |
| 2013/0041476 A1 | 2/2013 | Schulz |
| 2013/0053984 A1 | 2/2013 | Hunter et al. |
| 2013/0076699 A1 | 3/2013 | Spencer |
| 2013/0144197 A1 | 6/2013 | Ingimundarson et al. |
| 2013/0253705 A1 | 9/2013 | Goldfarb et al. |
| 2013/0268094 A1 | 10/2013 | Van Wiemeersch |
| 2014/0236314 A1 | 8/2014 | Van Wiemeersch |
| 2014/0324189 A1 | 10/2014 | Gill et al. |
| 2014/0371871 A1 | 12/2014 | Farina et al. |
| 2015/0142082 A1 | 5/2015 | Simon et al. |
| 2015/0216679 A1 | 8/2015 | Lipsey et al. |
| 2015/0216681 A1 | 8/2015 | Lipsey et al. |
| 2015/0230941 A1 | 8/2015 | Jury |
| 2015/0351935 A1 | 12/2015 | Donati et al. |
| 2015/0374515 A1 | 12/2015 | Meijer et al. |
| 2016/0120664 A1 | 5/2016 | Schultz |
| 2016/0143751 A1 | 5/2016 | Chestek et al. |
| 2016/0166409 A1 | 6/2016 | Goldfarb et al. |
| 2016/0250044 A1 | 9/2016 | Iversen et al. |
| 2016/0287422 A1 | 10/2016 | Kelly et al. |
| 2017/0007424 A1 | 1/2017 | Gill |
| 2017/0049583 A1 | 2/2017 | Belter et al. |
| 2017/0049586 A1 | 2/2017 | Gill et al. |
| 2017/0209288 A1 | 7/2017 | Veatch |
| 2017/0281368 A1 | 10/2017 | Gill |
| 2017/0340459 A1 | 11/2017 | Mandelbaum |
| 2018/0014744 A1 | 1/2018 | Duerstock et al. |
| 2018/0064563 A1 | 3/2018 | Gill |
| 2018/0071115 A1 | 3/2018 | Lipsey et al. |
| 2018/0116829 A1 | 5/2018 | Gaston et al. |
| 2018/0168477 A1 | 6/2018 | Graimann et al. |
| 2018/0221177 A1 | 8/2018 | Kaltenbach et al. |
| 2018/0235782 A1 | 8/2018 | Choi et al. |
| 2018/0256365 A1 | 9/2018 | Bai |
| 2018/0296368 A1 | 10/2018 | Gill |
| 2019/0091040 A1 | 3/2019 | Gill |
| 2019/0183661 A1 | 6/2019 | Gill |
| 2019/0216618 A1 | 7/2019 | Gill |
| 2020/0197193 A1 | 6/2020 | Byrne et al. |
| 2020/0268532 A1 | 8/2020 | Meijer et al. |

FOREIGN PATENT DOCUMENTS

| | | |
|---|---|---|
| DE | 309 367 | 11/1918 |
| DE | 24 34 834 | 2/1976 |
| DE | 198 54 762 | 6/2000 |
| DE | 101 05 814 | 9/2002 |
| DE | 203 15 575 | 1/2004 |
| DE | 10 2012 009 699 | 11/2013 |
| EP | 0 145 504 | 6/1985 |
| EP | 0 219 478 | 4/1987 |
| EP | 0 256 643 | 2/1988 |
| EP | 0 484 173 | 5/1992 |
| EP | 0 947 899 | 10/1999 |
| EP | 0 968 695 | 1/2000 |
| EP | 1 043 003 | 10/2000 |
| EP | 1 617 103 | 1/2006 |
| EP | 2 532 927 | 12/2012 |
| EP | 2 612 619 | 7/2013 |
| EP | 2 653 137 | 10/2013 |
| EP | 2 114316 | 7/2014 |
| EP | 2 125 091 | 4/2016 |
| EP | 2 467 101 | 4/2016 |
| EP | 2 696 814 | 1/2017 |
| GB | 326 970 | 3/1930 |
| GB | 607 001 | 2/1947 |
| GB | 1 386 942 | 3/1975 |
| GB | 1 510 298 | 5/1978 |
| GB | 1 585 256 | 2/1981 |
| GB | 2 067 074 | 7/1981 |
| GB | 2 146 406 | 4/1985 |
| GB | 2 357 725 A | 7/2001 |
| GB | 2 444 679 | 6/2008 |
| JP | 53-011456 | 2/1978 |
| JP | 53-094693 | 8/1978 |
| JP | 07-174631 | 7/1995 |
| JP | 2001-082913 | 3/2001 |
| JP | 2001-299448 | 10/2001 |
| JP | 2002-131135 | 5/2002 |
| JP | 2002-310242 | 10/2002 |
| JP | 2003-134526 | 5/2003 |
| JP | 2004-073802 | 3/2004 |
| JP | 2004-224280 | 8/2004 |
| WO | WO 95/024875 | 9/1995 |
| WO | WO 96/023643 | 8/1996 |
| WO | WO 00/025840 | 5/2000 |
| WO | WO 00/069375 | 11/2000 |
| WO | WO 01/004838 | 1/2001 |
| WO | WO 02/049534 | 6/2002 |
| WO | WO 03/017877 | 3/2003 |
| WO | WO 03/017878 | 3/2003 |
| WO | WO 03/017880 | 3/2003 |
| WO | WO 2006/058190 | 6/2006 |
| WO | WO 2006/069264 | 6/2006 |
| WO | WO 2006/078432 | 7/2006 |
| WO | WO 2006/086504 | 8/2006 |
| WO | WO 2006/092604 | 9/2006 |
| WO | WO 2006/110790 | 10/2006 |
| WO | WO 2007/063266 | 6/2007 |
| WO | WO 2007/076764 | 7/2007 |
| WO | WO 2007/076765 | 7/2007 |
| WO | WO 2007/126854 | 11/2007 |
| WO | WO 2007/127973 | 11/2007 |
| WO | WO 2008/044052 | 4/2008 |

(56) References Cited

FOREIGN PATENT DOCUMENTS

| WO | WO 2008/044207 | 4/2008 |
|---|---|---|
| WO | WO 2008/092695 | 8/2008 |
| WO | WO 2008/098059 | 8/2008 |
| WO | WO 2008/098072 | 8/2008 |
| WO | WO 2009/011682 | 1/2009 |
| WO | WO 2010/018358 | 2/2010 |
| WO | WO 2010/051798 | 5/2010 |
| WO | WO 2010/149967 | 12/2010 |
| WO | WO 2011/001136 | 1/2011 |
| WO | WO 2011/022569 | 2/2011 |
| WO | WO 2011/036473 | 3/2011 |
| WO | WO 2011/036626 | 3/2011 |
| WO | WO 2011/088964 | 7/2011 |
| WO | WO 2011/107778 | 9/2011 |
| WO | WO 2011/143004 | 11/2011 |
| WO | WO 2014/111843 | 7/2014 |
| WO | WO 2015/120076 | 8/2015 |
| WO | WO 2015/120083 | 8/2015 |
| WO | WO 2016/051138 | 4/2016 |
| WO | WO 2017/061879 | 4/2017 |
| WO | WO 2017/137930 | 8/2017 |
| WO | WO 2018/054945 | 3/2018 |
| WO | WO 2018/132711 | 7/2018 |
| WO | WO 2018/178420 | 10/2018 |
| WO | WO 2018/218129 | 11/2018 |

OTHER PUBLICATIONS

Antonio et al., "A Virtual Upper Limb Prosthesis as a Training System", 7th International Conference on Electrical Engineering, Computing Science and Automatic Control (CCE 2010) Tuxtla Gutiérrez, Chiapas, México. Sep. 8-10, 2010, pp. 210-215.
Bellman et al., "SPARKy 3: Design of an Active Robotic Ankle Prosthesis with Two Actuated Degrees of Freedom Using Regenerative Kinetics", in Proceedings of the 2nd Biennial IEEE/RAS-EMBS International Conference on Biomedical Robotics and Biomechatronics, Oct. 19-22, 2008, Scottsdale, AZ, pp. 511-516.
Belter et al., "Mechanical Design and Performance Specifications of Anthropomorphic Prosthetic Hands: A Review", JRRD, Jan. 2013, vol. 50, No. 5, pp. 599-618.
Biddiss et al., "Consumer Design Priorities for Upper Limb Prosthetics", Disability and Rehabilitation: Assistive Technology, Nov. 2007, vol. 2, No. 6, pp. 346-357.
Biddiss et al., "Upper Limb Prosthesis Use and Abandonment: A Survey of the Last 25 Years", Prosthetics and Orthotics International, Sep. 2007, vol. 31, No. 3, pp. 236-257.
Biddiss et al., "Upper-Limb Prosthetics: Critical Factors in Device Abandonment", American Journal of Physical Medicine & Rehabilitation, Dec. 2007, vol. 86, No. 12, pp. 977-987.
Chicoine et al., "Prosthesis-Guided Training of Pattern Recognition-Controlled Myoelectric Prosthesis", in Proceedings of the 34th Annual International Conference of the IEEE EMBS, San Diego, CA, Aug. 28-Sep. 1, 2012, pp. 1876-1879.
Childress et al., "Control of Limb Prostheses", American Academy of Orthopaedic Surgeons, Chapter 12, pp. 173-195, 2004.
Choi et al., "Design of High Power Permanent Magnet Motor with Segment Rectangular Copper Wire and Closed Slot Opening on Electric Vehicles", IEEE Transactions on Magnetics, Jun. 2010, vol. 46, No. 9, pp. 2070-2073.
Cipriani et al., "On the Shared Control of an EMG-Controlled Prosthetic Hand: Analysis of User-Prosthesis Interaction", IEEE Transactions on Robotics, Feb. 2008, vol. 24, No. 1, pp. 170-184.
Connolly, "Prosthetic Hands from Touch Bionics", Industrial Robot, Emerald Group Publishing Limited, 2008, vol. 35, No. 4, pp. 290-293.
Controzzi et al., "Miniaturized Non-Back-Drivable Mechanism for Robotic Applications", Mechanism and Machine Theory, Oct. 2010, vol. 45, No. 10, pp. 1395-1406.
Damian et al., "Artificial Tactile Sensing of Position and Slip Speed by Exploiting Geometrical Features", IEEE/ASME Transactions on Mechatronics, Feb. 2015, vol. 20, No. 1, pp. 263-274.

"DC Circuit Theory", https://www.electronics-tutorials.ws/docircuits/dcp_1.html, Date verified by the Wayback Machine Apr. 23, 2013, pp. 16.
Dechev et al., "Multiple Finger, Passive Adaptive Grasp Prosthetic Hand", Mechanism and Machine Theory, Oct. 1, 2001, vol. 36, No. 10, pp. 1157-1173.
Dellorto, Danielle, "Bionic Hands Controlled by iPhone App", CNN, Apr. 12, 2013, p. 4 http://www.cnn.com/2013/04/12/health/bionic-hands.
"DuPont Engineering Design—The Review of DuPont Engineering Polymers in Action", http://www.engpolymer.co.kr/x_data/magazine/engdesign07_2e.pdf, 2007, pp. 16.
Engeberg et al., "Adaptive Sliding Mode Control for Prosthetic Hands to Simultaneously Prevent Slip and Minimize Deformation of Grasped Objects," IEEE/ASME Transactions on Mechatronics, Feb. 2013, vol. 18, No. 1, pp. 376-385.
Fougner et al., "Control of Upper Limb Prostheses: Terminology and Proportional Myoelectric Control—A Review", IEEE Transactions on Neural Systems Rehabilitation Engineering, Sep. 2012, vol. 20, No. 5, pp. 663-677.
Fukuda et al., "Training of Grasping Motion Using a Virtual Prosthetic Control System", 2010 IEEE International Conference on Systems Man and Cybernetics (SMC), Oct. 10-13, 2010, pp. 1793-1798.
Gaine et al., "Upper Limb Traumatic Amputees. Review of Prosthetic Use", The Journal of Hand Surgery, Feb. 1997, vol. 22B, No. 1, pp. 73-76.
Grip Chips™, Datasheet, May 15, 2014, Issue 1, http://touchbionics.com/sites/default/files/files/Grip%20Chip%20datasheet%20May%202014.pdf, pp. 1.
Heckathorne, Craig W., "Components for Electric-Powered Systems", American Academy of Orthopaedic Surgeons, Chapter 11, pp. 145-171, 2004.
Hojjat et al., "A Comprehensive Study on Capabilities and Limitations of Roller-Screw with Emphasis on Slip Tendency", Mechanism and Machine Theory, 2009, vol. 44, No. 10, pp. 1887-1899.
Hsieh, Chiu-Fan., "Dynamics Analysis of Cycloidal Speed Reducers with Pinwheel and Nonpinwheel Designs", ASME Journal of Mechanical Design, Sep. 2014, vol. 136, No. 9, pp. 091008-1-091008-11.
Jebsen et al., "An Objective and Standardized Test of Hand Function", Archives of Physical Medicine and Rehabilitation, Jun. 1969, vol. 50, No. 6, pp. 311-319.
Johannes et al., "An Overview of the Developmental Process for the Modular Prosthetic Limb," John Hopkins APL Technical Digest, 2011, vol. 30, No. 3, pp. 207-216.
Kent et al., "Electromyogram Synergy Control of a Dexterous Artificial Hand to Unscrew and Screw Objects", Journal of Neuroengineering and Rehabilitation, 2014, vol. 11, No. 1, pp. 1-20.
Kermani et al., "Friction Identification and Compensation in Robotic Manipulators", IEEE Transactions on Instrumentation and Measurement, Dec. 2007, vol. 56, No. 6, pp. 2346-2353.
Kuiken et al., "Targeted Muscle Reinnervation for Real-Time Myoelectric Control of Multifunction Artificial Arms", JAMA, Feb. 11, 2009, vol. 301, No. 6, pp. 619-628.
Kyberd et al., "Two-Degree-of-Freedom Powered Prosthetic Wrist", Journal of Rehabilitation Research & Development, 2011, vol. 48, No. 6, pp. 609-617.
Lamounier et al., "On the Use of Virtual and Augmented Reality for Upper Limb Prostheses Training and Simulation", 2010 Annual International Conference of the IEEE Engineering in Medicine and Biology Society (EMBC), Aug. 31-Sep. 4, 2010, pp. 2451-2454.
Light et al., "Establishing a Standardized Clinical Assessment Tool of Pathologic and Prosthetic Hand Function: Normative Data, Reliability, and Validity", Archives of Physical Medicine and Rehabilitation, Jun. 2002, vol. 83, pp. 776-783.
Mace et al., "Augmenting Neuroprosthetic Hand Control Through Evaluation of a Bioacoustic Interface", IEEE/RSJ International Conference on Intelligent Robots and Systems (IROS), Tokyo, Japan, Nov. 3-7, 2013, pp. 7.
Majd et al., "A Continuous Friction Model for Servo Systems with Stiction", in Proceedings of the IEEE Conference on Control Applications, 1995, pp. 296-301.

(56) References Cited

OTHER PUBLICATIONS

Martinez-Villalpando et al., "Agonist-Antagonist Active Knee Prosthesis: A Preliminary Study in Level-Ground Walking", Journal of Rehabilitation Research & Development, vol. 46, No. 3, 2009, pp. 361-374.
Maxon Precision Motors, Inc., "Maxon Flat Motor: EX 10 flat 10 mm, brushless, 0.25 Watt", Specification, May 2011, p. 181.
Maxon Precision Motors, Inc., "Maxon EC Motor: EC10 10 mm, brushless, 8 Watt", Specification, May 2011, p. 140.
Miller et al., "Summary and Recommendations of the Academy's State of the Science Conference on Upper Limb Prosthetic Outcome Measures", Journal of Prosthetics Orthotics, 2009, vol. 21, pp. 83-89.
Montagnani et al., "Is it Finger or Wrist Dexterity that is Missing in Current Hand Prostheses?", IEEE Transactions on Neural Systems and Rehabilitation Engineering, Jul. 2015, vol. 23, No. 4, pp. 600-609.
Morita et al., "Development of 4-D.O.F. Manipulator Using Mechanical Impedance Adjuster", Proceedings of the 1996 IEEE International Conference on Robotics and Automation, Minneapolis, MN, Apr. 1996, pp. 2902-2907.
Ninu et al., "Closed-Loop Control of Grasping with a Myoelectric Hand Prosthesis: Which are the Relevant Feedback Variable for Force Control?" IEEE Transactions on Neural Systems and Rehabilitation Engineering, Sep. 2014, vol. 22, No. 5, pp. 1041-1052.
Osborn et al., "Utilizing Tactile Feedback for Biomimetic Grasping Control in Upper Limb Prostheses". Department of Biomedical Engineering, Johns Hopkins University, Baltimore, USA, 2013, pp. 4.
Pedrocchi et al., "MUNDUS Project: Multimodal Neuroprosthesis for Daily Upper Limb Support", Journal of Neuroengineering and Rehabilitation, 2013, vol. 10, No. 66, pp. 20. http://www.jneuroengrehab.com/content/10/1/66.
Pinzur et al., "Functional Outcome Following Traumatic Upper Limb Amputation and Prosthetic Limb Fitting", J. Hand Surgery, Amer. vol., 1994. vol. 19, pp. 836-839.
Press Release, "Touch Bionics Introduce Digitally Controlled Supro Wrist", http://www.touchbionics.com/news-events/news/touch-bionics-introduce-digitally-controlled-supro-wrist, May 3, 2016 in 2 pages.
Raspopovic et al., "Restoring Natural Sensory Feedback in Real-Time Bidirectional Hand Prostheses", Science Translational Medicine, Feb. 5, 2014, vol. 6, No. 222, pp. 1-10.
Resnik et al., "The DEKA Arm: Its Features, Functionality, and Evolution During the Veterans Affairs Study to Optimize the DEKA Arm", Prosthetics and Orthotics International, 2014, vol. 38, No. 6, pp. 492-504.
Scheme et al., "Electromyogram Pattern Recognition for Control of Powered Upper-Limb Prostheses: State of the Art and Challenges for Clinical Use", Journal of Rehabilitation Research & Development (JRRD), 2011, vol. 48, No. 6, pp. 643-659.
Scheme et al., "Motion Normalized Proportional Control for Improved Pattern Recognition-Based Myoelectric Control", IEEE Transactions on Neural Systems and Rehabilitation Engineering, Jan. 2014, vol. 22, No. 1, pp. 149-157.
Sensinger et al., "Cycloid vs. Harmonic Drives for use in High Ratio, Single Stage Robotic Transmissions", 2012 IEEE Conference on Robotics and Automation (ICRA), Saint Paul, MN, USA, May 14-18, 2012, pp. 4130-4135.
Sensinger, "Efficiency of High-Sensitivity Gear Trains, such as Cycloid Drives", Journal of Mechanical Design, Jul. 2013, vol. 135, No. 7, pp. 071006-1-071006-9.
Sensinger et al., "Exterior vs. Interior Rotors in Robotic Brushless Motors", 2011 IEEE International Conference on Robotics and Automation (ICRA), Shanghai, China, May 9-13, 2011, pp. 2764-2770.
Sensinger, "Selecting Motors for Robots Using Biomimetic Trajectories: Optimum Benchmarks, Windings, and other Considerations," 2010 IEEE International Conference on Robotics and Automation (ICRA), Anchorage, AL, USA, May 3-8, 2010, pp. 4175-4181.
Sensinger, "Unified Approach to Cycloid Drive Profile, Stress, and Efficiency Optimization", Journal of Mechanical Design, Feb. 2010, vol. 132, pp. 024503-1-024503-5.
Sensinger et al., "User-Modulated Impedance Control of a Prosthetic Elbow in Unconstrained, Perturbed Motion", IEEE Transactions on Biomedical Engineering, Mar. 2008, vol. 55, No. 3, pp. 1043-1055.
Stix, Gary, "Phantom Touch: Imbuing a Prosthesis with Manual Dexterity", Scientific American, Oct. 1998, pp. 41 & 44.
"Supro Wrist", Touch Bionics, https://web.archive.org/web/20160928141440/http://www.touchbionics.com/products/supro-wrist as archived Sep. 28, 2016 in 3 pages.
Sutton et al., "Towards a Universal Coupler Design for Modern Powered Prostheses", MEC 11 Raising the Standard, Proceedings of the 2011 MyoElectric Controls/Powered Prosthetics Symposium Frederiction, New Brunswick, Canada, Aug. 14-19, 2011, pp. 5.
Tan et al., "A Neural Interface Provides Long-Term Stable Natural Touch Perception", Science Translational Medicine, Oct. 2014, vol. 6, No. 257, pp. 1-11.
Tang, "General Concepts of Wrist Biomechanics and a View from Other Species", The Journal of Hand Surgery, European Volume Aug. 2008, vol. 33, No. 4, pp. 519-525.
Toledo et al., "A Comparison of Direct and Pattern Recognition Control for a Two Degree-of-Freedom Above Elbow Virtual Prosthesis", in Proceedings 34th Annual International Conference of the IEEE EMBS, 2012, pp. 4332-4335.
"Touch Bionics Grip Chips Let Hand Prostheses Think for Themselves", May 15, 2014, www.medgadget.com/2014/05/touch-bionics-grip-chips-let-hand-prostheses-think-for-themselves.html, pp. 2.
Touch Bionics PowerPoint Presentation in 3 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).
Touch Bionics PowerPoint Slide in 1 page, believed to be presented at Advanced Arm Dynamics company Jan. 11, 2016. (Applicant requests that the Examiner consider this reference as qualifying as prior art as of the date indicated, but Applicant does not admit its status as prior art by submitting it here and reserves the right to challenge the reference's prior art status at a later date).
Touch Bionics Screenshots of video in PowerPoint Presentation in 4 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).
Trachtenberg et al., "Radio Frequency Identification, An Innovative Solution to Guide Dexterous Prosthetic Hands", 33rd Annual International Conference of the IEEE EMBS, Boston, MA, Aug. 30-Sep. 3, 2011, pp. 4.
Vilarino, Martin, "A Novel Wireless Controller for Switching among Modes for an Upper-Limb Prosthesis", The Academy Today, Jan. 2014, vol. 10, No. 1, pp. A-12 to A-15.
Weir et al., "Design of Artificial Arms and Hands for Prosthetic Applications", Biomedical Engineering and Design Handbook, 2009, vol. 2, pp. 537-598.
Wettels et al., "Grip Control Using Biomimetic Tactile Sensing Systems", IEEE/ASME Transactions on Mechatronics, Dec. 2009, vol. 14, No. 6, pp. 718-723.
Whiteside et al., "Practice Analysis Task Force: Practice Analysis of the Disciplines of Orthotics and Prosthetics", American Board for Certification in Orthotics and Prosthetics, Inc., 2000, pp. 1-51.
Wilson et al., "A Bus-Based Smart Myoelectric Electrode/Amplifier-System Requirements", IEEE Transactions on Instrumentation and Measurement, Oct. 2011, vol. 60, No. 10, pp. 3290-3299.
Zampagni et al., "A Protocol for Clinical Evaluation of the Carrying Angle of the Elbow by Anatomic Landmarks", Journal of Shoulder and Elbow Surgery, 2008, vol. 17, No. 1, pp. 106-112.

(56) References Cited

OTHER PUBLICATIONS

International Search Report and Written Opinion in Application No. PCT/GB2010/001232, dated Oct. 10, 2010.
International Preliminary Report on Patentability and Written Opinion in Application No. PCT/GB2010/001232, dated Jan. 4, 2012.
International Search Report and Written Opinion in Application No. PCT/GB2012/052111, dated Nov. 26, 2012.
International Search Report and Written Opinion in Application No. PCT/GB2012/052021, dated Nov. 26, 2012.
International Preliminary Report on Patentability and Written Opinion in Application No. PCT/GB2012/052021, dated Feb. 27, 2014.
International Search Report and Written Opinion in Application No. PCT/GB2010/051529, dated Jan. 4, 2011.
International Preliminary Report on Patentability and Written Opinion in Application No. PCT/GB2010/051529, dated Apr. 5, 2012.
International Search Report and Written Opinion in Application No. PCT/GB2013/051961, dated Dec. 11, 2013.
Baek et al., "Design and Control of a Robotic Finger for Prosthetic Hands", Proceedings of the 1999 IEEE International Conference on Intelligent Robots and Systems, pp. 113-117.
Butterfaß et al., "DLR-Hand II: Next Generation of a Dextrous Robot Hand", IEEE International Conference on Robotics and Automation, Seoul, Korea, May 21-26, 2001, vol. 1, pp. 109-114.
Cotton et al., "Control Strategies for a Multiple Degree of Freedom Prosthetic Hand", Measurement + Control, Feb. 2007, vol. 40, No. 1, pp. 24-27.
"DsPIC Microcontrollers Introduction and Features", https://microcontrollerslab.com/dspic-microcontrollers-introduction/, Aug. 1, 2017, pp. 4.
Edsinger-Gonzales, Aaron, "Design of a Compliant and Force Sensing Hand for a Humanoid Robot", 2005, pp. 5.
Fildes, Jonathan, "Bionic Hand Wins Top Tech Prize", BBC News, Jun. 9, 2008, http://news.bbc.co.uk/2/hi/science/nature/7443866.stm, pp. 3.
Gaiser et al., "A New Anthropomorphic Robotic Hand", 2008 8th IEEE-RAS International Conference on Humanoid Robots, Dec. 1-3, 2008, Daejeon, Korea, pp. 418-422.
"ILimb Bionic Hand Now Ready for Market", Technovelgy.com, www.technovelgy.com/ct/Science-Fiction-News.asp?NewsNum=1125, as printed Jul. 6, 2020 in 3 pages.
International Preliminary Report on Patentability and Written Opinion in Application No. PCT/IB2016/001713, dated Mar. 5, 2019.
Kargov et al., "Applications of a Fluidic Artificial Hand in the Field of Rehabilitation", Rehabilitation Robotics, Ch. 15, Aug. 2007, pp. 261-286.
Kargov et al., "Development of a Multifunctional Cosmetic Prosthetic Hand", Proceedings for the 2007 IEEE 10th International Conference on Rehabilitation Robotics, Jun. 12-15, 2007, Noordwijk, The Netherlands, pp. 550-553.
Kargov et al., "Modularly Designed Lightweight Anthropomorphic Robot Hand", 2006 IEEE International Conference on Multisensor Fusion and Integration for Intelligent Systems, Sep. 3-6, 2006, Heidelberg, Germany, pp. 155-159.
Kawasaki et al., "Design and Control of Five-Fingered Haptic Interface Opposite to Human Hand", IEEE Transactions on Robotics, Oct. 2007, vol. 23, No. 5., pp. 909-918.
Lotti et al., "UBH 3: A Biologically Inspired Robotic Hand", Jan. 2004, pp. 7.
MEC '05: Integrating Prosthetics and Medicine, University of New Brunswick's MyoElectric Controls/Powered Prosthetics Symposium, Aug. 17-19, 2005, Fredericton NB Canada, pp. 260.
Poppe, Zytel HTN Provides a Helping Hand, DuPont Engineering Design 8 (2007), pp. 3.
Puig et al., "A Methodology for the Design of Robotic Hands with Multiple Fingers", International Journal of Advanced Robotic Systems, 2008, vol. 5, No. 2, pp. 177-184.
Pylatiuk et al., "Design and Evaluation of a Low-Cost Force Feedback System for Myoelectric Prosthetic Hands", 18 J. Prosthetics and Orthotics 57-61 (2006).
Pylatiuk et al., "Results of an Internet Survey of Myoelectric Prosthetic Hand Users", Prosthetics and Orthotics International, Dec. 2007, vol. 31, No. 4, pp. 362-370.
Ryew et al., "Robotic Finger Mechanism with New Anthropomorphic Metacarpal Joint", 26th Annual Conference of the IEEE Industrial Electronics Society, 2000. IECON 2000, vol. 1, pp. 416-421.
Schulz et al., "Die Entwicklung Einer Multifunktionalen Kosmetischen Handprothese", Prothetik, Orthopädie-Technik, Aug. 2006, pp. 627-632.
The Weir Thesis ("Weir Thesis") is entitled "An Externally-Powered, Myo-Electrically Controlled Synergetic Prosthetic Hand for the Partial-Hand Amputee", published Aug. 1989, pp. 365. [Uploaded in 3 Parts].
Ward, Derek Kempton, "Design of a Two Degree of Freedom Robotic Finger", Sep. 1996, pp. 155.
Weir et al., "A Myoelectrically Controlled Prosthetic Hand for Transmetacarpal Amputations", JPO Journal of Prosthetics and Orthotics, Jun. 2001, vol. 13, No. 2, pp. 26-31.
Weir et al., "The Design and Development of a Synergetic Partial Hand Prosthesis with Powered Fingers", RESNA '89, Proceedings of the 12th Annual Conference, Technology for the Next Decade, Jun. 25-30, 1989, pp. 473-474.
"World's First Bionic Hand Factory Opened by Scottish Company", DailyMail.com, Jan. 8, 2008, https://www.dailymail.co.uk/sciencetech/article-506661/Worlds-bionic-hand-factory-opened-Scottish-company.html, pp. 4.

\* cited by examiner

PROSTHETIC FEEDBACK APPARATUS AND METHOD

CROSS REFERENCE TO RELATED APPLICATIONS

This application is a continuation of U.S. patent application Ser. No. 14/235,282, filed May 13, 2014, entitled "Prosthetic Feedback Apparatus and Method," which is a U.S. national stage application of International Patent App. No. PCT/GB2012/052021, filed Aug. 17, 2012, which claims priority to and benefit of G.B. App. No. 1114264.3, filed Aug. 18, 2011, entitled "Improvements in or relating to Prosthetics and Orthotics," each of which is hereby incorporated herein by reference in its entirety.

BACKGROUND

Field

The present invention relates to a moveable component of a prosthesis or an orthosis and a method of operating the same.

Description of Related Art

Prosthetic hands with powered digits are known. For example, International Pub. Nos. WO 2007/063266 and WO 2010/149967 disclose a prosthesis with a mechanically operable digit member that is moved by an electric motor. International Pub. No. WO 2010/149967 discloses a method of controlling the operation of the digit member to increase the force applied 10 thereby to an object.

The present inventor has appreciated shortcomings with known prostheses having motor driven digit members, such as those disclosed in International Pub. Nos. WO 2007/063266 and WO 2010/149967.

SUMMARY

According to a first aspect of the present invention there is provided a prosthesis or an orthosis comprising:
a moveable component; a motor operable to move the component, wherein the motor has at least 20 one operating parameter, the application of which to the motor results in the component having at least one operating condition; and an electronic device operable to:
determine at least one operating parameter of the motor; and
determine at least one instantaneous operating condition of the component from a predetermined operating profile of the motor and component and the determined at least one operating parameter of the motor, the predetermined operating profile of the motor and component being based on one or more operating parameter inputs to the motor and one or more resulting operating condition outputs of the component.

The electronic device may be operable to determine at least one instantaneous operating parameter of the motor.

The predetermined operating profile of the motor and component may be based on a plurality of operating parameter inputs to the motor and a plurality of resulting operating condition outputs of the component.

The motor may be located inside the component.

The component may be a digit of a hand prosthesis. The component may be a finger or a thumb member of hand prosthesis. The motor may be located inside the digit 10 of the hand prosthesis.

The component may be moveable with respect to a support body of the prosthesis or orthosis. The component may rotate and/or pivot with respect to the support body of the prosthesis or orthosis.

The motor may be an electric motor. The motor may be a direct current motor. The motor may be an AC motor, a DC motor, a brushed or brushless motor, a servo motor, a stepper motor, a linear motor or a worm gear motor.

The at least one operating parameter of the motor may include an electrical signal. The electrical signal may be in the form of an applied electrical current and/or voltage.

The at least one operating parameter of the motor may include the electrical signal passing through the motor. The at least one operating parameter of the motor determined by the electronic device may include the current drawn by the motor and/or the voltage drop across the motor.

The electrical signal may comprise a plurality of spaced apart pulses.

The electronic device may include a circuit board containing electronic circuitry which is operable to apply the at least one operating parameter to the motor. The electronic circuitry may be operable to provide bi-directional drive of the motor.

The motor may be operable via one or more switches. The switches may be actuated by residual movement of the wearer of the prosthesis or orthosis, wrist and/or shoulder movement of the wearer of the prosthesis or orthosis, or the like. Alternatively, or additionally, the motor may be operable via signals derived from the activity of, or from, electromyographic (EMG) activity of residual muscle actions of the wearer of the prosthesis or orthosis, pressure sensitive resistors on the wearer of the prosthesis or orthosis, signals derived from one or more neural implants in the wearer of the prosthesis or orthosis, EMG activity from reinnervated muscles, muscles of the feet and/or chest, or the like.

The at least one operating condition of the component may include one or more of the group consisting of: initial movement, contact of the component with a surface, slipping or sliding of the component with a surface, acceleration, deceleration, average speed, instantaneous speed, amount of extension, amount of flexion, and force applied by the component to a surface.

The electronic device may, in addition to being operable to determine an instantaneous operating condition of the component, be operable to determine an historic operating condition of the component. That is, the electronic device may be operable to determine historical actions performed by the component. From a knowledge of the instantaneous operating condition of the component and a knowledge of the historical operating conditions of the component the electronic device may be further operable to determine a change in any of the conditions, an average of any of the conditions, a forecasted or requested operating condition.

The at least one operating condition of the component may also include the relative position of the component. The relative position of the component may be one dimensional, two dimensional or three dimensional. The operating condition of the component may also include the angle of the component, or a part thereof, to a reference plane, axis or point. The operating condition of the component may also include the distance between at least two components, such as a finger and thumb. The position of the component may be determined from a knowledge of the starting position or end position of the component, the duration of applied operating signal and the speed of travel of the component.

The at least one operating condition of the component may also include conditions derived from any of the above-referenced conditions, such as a change in any of the 10 conditions, or an average of any of the conditions.

The at least one operating condition of the component may also include one or more previous operating conditions, one or more forecasted and/or requested operating conditions.

The at least one operating condition of the component may include a combination of any of the group consisting of: initial movement, contact of the component with a surface, slipping or sliding of the component with a surface, acceleration, deceleration, average speed, instantaneous speed, amount of extension, amount of flexion, and force applied by the component to a surface.

The operating conditions described above may relate to the component as a whole or at least part of the component.

The electronic device may be operable to determine the instantaneous electrical signal applied to the motor. The electronic device may be operable to determine the instantaneous current and/or voltage applied to the motor. The electronic device may be operable to determine the instantaneous current drawn by the motor and/or the voltage drop across the motor. The current drawn by the motor for any applied operating voltage is dependent upon the load placed on the motor. The current drawn by the motor thus varies with respect to load placed thereupon.

The electronic device may include a circuit board containing electronic circuitry which is operable to measure the instantaneous operating parameter of the motor. The electronic circuitry may include a current and/or voltage measurement circuit.

The electronic device may include a memory device operable to store the predetermined operating profile of the motor and component.

The electronic device may include firmware operable to map the determined at least one instantaneous operating parameter of the motor to the predetermined operating profile of the motor and component. The electronic device may include firmware operable to compare the determined at least one instantaneous operating parameter of the motor with the predetermined operating profile of the motor and component.

The electronic device may include firmware operable to determine the at least one instantaneous operating condition of the component from the predetermined operating profile of the motor and component. The firmware may include a computer program stored in the memory of the firmware.

The predetermined operating profile of the motor and component may include one or more data sets representative of one or more operating parameter inputs to the motor and one or more resulting operating condition outputs of the component. The operating profile of the motor and component may be obtained by characterising the operation of the component as a function of operating parameter inputs to the motor. The operating profile of the motor and component may include one or more data sets representative of the instantaneous operating parameter of the motor as a function of the instantaneous operating condition of the component.

The predetermined operating profile of the motor and component may include one or more data sets representative of at least one of the following operating conditions of the component: initial movement, contact of the component with a surface, slipping or sliding of the component with a surface, acceleration, deceleration, average speed, instantaneous speed, amount of extension, amount of flexion, and force applied by the component to a surface; and corresponding operating parameters of the motor. The predetermined operating profile of the motor and component may include one or more data sets representative of the instantaneous operating conditions of the component listed above and one or more of the instantaneous operating parameters of the motor.

The predetermined operating profile of the motor and component may be obtained by characterising the operation of the motor as a function of one or more operating conditions of the component. The component may be instructed to perform one or more of the above-listed operating conditions and the resulting operating parameters of the motor measured. The current drawn by the motor and/or the voltage drop across the motor may be determined as the component carries out its instructed task. This characterising of the motor and component may be carried out over one or more of the above-listed operating conditions of the component.

The predetermined operating profile of the motor and component may be determined by a mathematical model based on the one or more operating parameter inputs to the motor and the one or more resulting operating condition outputs of the component. The mathematical model may be a mathematical function, numerical mapping, or the like. The mathematical model may be a neural network, an artificial neural network, decision tree (D T), support vector Machine (SVM), logistic regression (LR), other such "machine learning" techniques.

The electronic device may be further operable to produce an output signal indicative of the determined at least one instantaneous operating condition of the component.

The electronic device may be operable to produce an output signal indicative of one or more of the determined instantaneous operating conditions in the group consisting of: initial movement, contact of the component with a surface, slipping or sliding of the component with a surface, acceleration, deceleration, average speed, instantaneous speed, amount of extension, amount of flexion, and force applied by the component to a surface.

The electronic device may, in addition to being operable to produce an output signal indicative of one or more determined instantaneous operating conditions of the component, be operable to produce an output signal indicative of one or more historic operating conditions of the component. That is, the electronic device may be operable to produce an output signal indicative one or more historical actions performed by the component. From a knowledge of the instantaneous operating condition of the component and a knowledge of the historical operating conditions of the component the electronic device may be further operable to produce an output signal indicative of a change in any of the conditions, an average of any of the conditions, a forecasted or requested operating condition.

The electronic device may be operable to produce an output signal indicative of the relative position of the component. The relative position of the component may be one dimensional, two dimensional or three dimensional. The electronic device may be operable to produce an output signal indicative of the angle of the component, or a part thereof, to a reference plane, axis or point. The electronic device may be operable to produce an output signal indicative of the distance between at least two components, such as a finger and thumb.

The electronic device may be operable to produce an output signal indicative of conditions derived from any of the above-referenced conditions, such as a change in any of the conditions, or an average of any of the conditions.

The electronic device may be operable to produce an output signal indicative of one or more previous operating conditions, one or more forecasted and/or requested operating conditions.

The electronic device may be operable to produce an output signal indicative of a combination of any of the group consisting of: initial movement, contact of the component with a surface, slipping or sliding of the component with a surface, acceleration, deceleration, average speed, instantaneous speed, amount of extension, amount of flexion, and force applied by the component to a surface.

The electronic device may be further operable to produce an output signal indicative of a plurality of determined instantaneous operating conditions of the component.

The output signal may be indicative of a general operating condition of the component. The general operating condition of the component may include one or more modes of operation and/or configurations.

The electronic device may be further operable to produce an output signal which is indicative of a requested operating condition of the component from the wearer of the prosthesis or orthosis. The electronic device may be further operable to produce an output signal which is indicative of a completed operating condition of the component from the wearer of the prosthesis or orthosis.

The electronic device may be further operable to use the output signal together with the operating parameters of the motor in a control strategy for the operation of the component. The electronic device may be further operable to use the output signal together with the operating parameters of the motor to control the operation of the component. For example, the output signal may indicate the relative position of the component and the electronic device may modify the operating parameter of the motor based on the output signal to achieve a requested position of the component, or the output signal may indicate the force exerted by the component on an object and the electronic device may modify the operating parameter of the motor based on the output signal to achieve a requested force from the component.

Additionally, or alternatively, the electronic device may be further operable to communicate the output signal to the wearer of the prosthesis or orthosis.

The output signal may be communicated to the wearer of the prosthesis or orthosis visually, kinaesthetically, aurally or neurally.

The output signal may be communicated to the wearer of the prosthesis or orthosis in one or more combinations of the above forms of communication.

The output signal is thus fed back to the wearer of the prosthesis or orthosis. The mode of feedback to the wearer of the prosthesis or orthosis may include vibrotactile or electrotactile.

The output signal may be fed back to the wearer of the prosthesis or orthosis at a stump, arm or healthy hand, shoulder, neck, foot, tongue, or the like.

In this arrangement the wearer of the prosthesis or orthosis receives a signal from the electronic device which indicates to them an instantaneous operating condition of the component. Thus, for example, the wearer of the prosthesis or orthosis receives a feedback signal from the prosthesis or orthosis which indicates the current force being applied by the component to a surface or object. The wearer therefore knows if the current force being applied to the surface or object is suitable for their needs, or if a greater or lesser force is required. For example, if the wearer is trying to push a button with the component of the prosthesis, they will receive a feedback signal which indicates to them if the component is pressing against the button with sufficient force to allow the button to be depressed. Also, if the wearer is trying to move an object with the component of the prosthesis, they may receive a feedback signal which indicates to them if the component is pushing, pulling, squeezing or lifting the object with sufficient force to allow the object to be moved.

This is just one example of the information which may be fed back to the wearer. It should be appreciated that the output signal fed back to the wearer of the prosthesis or orthosis may include more than one instantaneous operating condition of the component.

The prosthesis or orthosis may comprise a plurality of moveable components, with each component having a motor and electronic device.

Alternatively, the prosthesis or orthosis may comprise a plurality of moveable components, with each motor having a motor, but only a single electronic device. In this arrangement the electronic device may be operable to determine the instantaneous operating parameters of each motor, map the instantaneous operating parameter of each motor to a predetermined operating profile of each motor and component, and determine the instantaneous operating condition of each component from the predetermined operating profile of each motor and component.

The prosthesis or orthosis may comprise one or more first components acting as fingers and second component acting as a thumb. In this arrangement the electronic device may be further operable to determine the grasp aperture between the fingers and thumb and undesired movement between the component and an object, i.e. a slip condition, between the fingers and thumb when each component is bearing against a surface or object. The grasp aperture and slip condition here being examples of operating conditions of the components.

According to a second aspect of the present invention there is provided a method of operating a prosthesis or orthosis having a moveable component, a motor operable to move the component, wherein the motor has at least one operating parameter, the application of which to the motor results in the component having at least one operating condition, and an electronic device, the method comprising the steps of:

applying at least one operating parameter to the motor; and using the electronic device to:

determine at least one operating parameter of the motor; and determine at least one instantaneous operating condition of the component from a predetermined operating profile of the motor and component and the determined at least one operating parameter of the motor, the predetermined operating profile of the motor and component being based on one or more operating parameter inputs to the motor and one or more resulting operating condition outputs of the component.

The electronic device may be operable to determine at least one instantaneous operating parameter of the motor.

The predetermined operating profile of the motor and component may be based on a plurality of operating parameter inputs to the motor and a plurality of resulting operating condition outputs of the component.

The motor may be located inside the component.

The component may be a digit of a hand prosthesis. The component may be a finger or a thumb member of hand prosthesis. The motor may be located inside the digit of the hand prosthesis.

The component may be moveable with respect to a support body of the prosthesis or orthosis. The component may rotate and/or pivot with respect to the support body of the prosthesis or orthosis.

The motor may be an electric motor. The motor may be a direct current motor. The motor may be an AC motor, a DC motor, a brushed or brushless motor, a servo motor, a stepper motor, a linear motor or a worm gear motor.

The at least one operating parameter of the motor may include an electrical signal. The electrical signal may be in the form of an applied electrical current and/or voltage.

The at least one operating parameter of the motor may include the electrical signal passing through the motor. The at least one operating parameter of the motor determined by the electronic device may include the current drawn by the motor and/or the voltage drop across the motor.

The electrical signal may comprise a plurality of spaced apart pulses.

The electronic device may include a circuit board containing electronic circuitry which is operable to apply the at least one operating parameter to the motor. The electronic circuitry may be operable to provide bi-directional drive of the motor.

The motor may be operable via one or more switches. The switches may be actuated by residual movement of the wearer of the prosthesis or orthosis, wrist and/or shoulder movement of the wearer of the prosthesis or orthosis, or the like. Alternatively, or additionally, the motor may be operable via signals derived from the activity of, or from, electromyographic (EMG) activity of residual muscle actions of the wearer of the prosthesis or orthosis, pressure sensitive resistors on the wearer of the prosthesis or orthosis, signals derived from one or more neural implants in the wearer of the prosthesis or orthosis, EMG activity from reinnervated muscles, muscles of the feet and/or chest, or the like.

The method may comprise the further step of using residual movement of the wearer of the prosthesis or orthosis, wrist and/or shoulder movement of the wearer of the prosthesis or orthosis to apply the at least one operating parameter to the motor. The method may comprise the further step of using signals derived the activity of, or from, electromyographic (EMG) activity of residual muscle actions of the wearer of the prosthesis or orthosis, pressure sensitive resistors on the wearer of the prosthesis or orthosis, signals derived from one or more neural implants in the wearer of the prosthesis or orthosis, EMG activity from reinnervated muscles, muscles of the feet and/or chest to apply the at least one operating parameter to the motor.

The at least one operating condition of the component may include one or more of the group consisting of: initial movement, contact of the component with a surface, slipping or sliding of the component with a surface, acceleration, deceleration, average speed, instantaneous speed, amount of extension, amount of flexion, and force applied by the component to a surface.

The electronic device may, in addition to being operable to determine an instantaneous operating condition of the component, be operable to determine an historic operating condition of the component. That is, the electronic device may be operable to determine historical actions performed by the component. From a knowledge of the instantaneous operating condition of the component and a knowledge of the historical operating conditions of the component the electronic device may be further operable to determine a change in any of the conditions, an average of any of the conditions, a forecasted or requested operating condition.

The at least one operating condition of the component may also include the relative position of the component. The relative position of the component may be one dimensional, two dimensional or three dimensional. The operating condition of the component may also include the angle of the component, or a part thereof, to a reference plane, axis or point. The operating condition of the component may also include the distance between at least two components, such as a finger and thumb.

The at least one operating condition of the component may also include conditions derived from any of the above-referenced conditions, such as a change in any of the conditions, or an average of any of the conditions.

The at least one operating condition of the component may also include one or more previous operating conditions, one or more forecasted and/or requested operating conditions.

The at least one operating condition of the component may include a combination of any of the group consisting of: initial movement, contact of the component with a surface, slipping or sliding of the component with a surface, acceleration, deceleration, average speed, instantaneous speed, amount of extension, amount of flexion, and force applied by the component to a surface.

The operating conditions described above may relate to the component as a whole or at least part of the component.

The electronic device may be operable to determine the instantaneous electrical signal applied to the motor. The electronic device may be operable to determine the instantaneous current and/or voltage applied to the motor. The electronic device may be operable to determine the instantaneous current drawn by the motor and/or the voltage drop across the motor. The current drawn by the motor for any applied operating voltage is dependent upon the load placed on the motor. The current drawn by the motor thus varies with respect to load placed thereupon.

The method may comprise the further step of using the electronic device to determine the instantaneous electrical signal applied to the motor.

The electronic device may include a circuit board containing electronic circuitry which is operable to measure the instantaneous operating parameter of the motor.

The electronic circuitry may include a current and/or voltage measurement circuit.

The electronic device may include a memory device operable to store the predetermined operating profile of the motor and component.

The electronic device may include firmware operable to map the determined at least one instantaneous operating parameter of the motor to the predetermined operating profile of the motor and component. The electronic device may include firmware operable to compare the determined at least one instantaneous operating parameter of the motor with the predetermined operating profile of the motor and component.

The electronic device may include firmware operable to determine the at least one instantaneous operating condition of the component from the predetermined operating profile of the motor and component. The firmware may include a computer program stored in the memory of the firmware.

The predetermined operating profile of the motor and component may include one or more data sets representative of one or more operating parameter inputs to the motor and one or more resulting operating condition outputs of the component. The operating profile of the motor and component may be obtained by characterising the operation of the component as a function of operating parameter inputs to the motor. The operating profile of the motor and component may include one or more data sets representative of the instantaneous operating parameter of the motor as a function of the instantaneous operating condition of the component.

The predetermined operating profile of the motor and component may include one or more data sets representative of at least one of the following operating conditions of the component: initial movement, contact of the component with a surface, slipping or sliding of the component with a surface, acceleration, deceleration, average speed, instantaneous speed, amount of extension, amount of flexion, and force applied by the component to a surface; and corresponding operating parameters of the motor. The predetermined operating profile of the motor and component may include one or more data sets representative of the instantaneous operating conditions of the component listed above and one or more of the instantaneous operating parameters of the motor.

The predetermined operating profile of the motor and component may be obtained by characterising the operation of the motor as a function of one or more operating conditions of the component. The component may be instructed to perform one or more of the above-listed operating conditions and the resulting operating parameters of the motor measured. The current drawn by the motor and/or the voltage drop across the motor may be determined as the component carries out its instructed task. This characterising of the motor and component may be carried out over one or more of the above-listed operating conditions of the component.

The predetermined operating profile of the motor and component may be determined by a mathematical model based on the one or more operating parameter inputs to the motor and the one or more resulting operating condition outputs of the component. The mathematical model may be a mathematical function, numerical mapping, or the like. The mathematical model may be a neural network, an artificial neural network, decision tree (D T), support vector Machine (SVM), logistic regression (LR), other such "machine learning" techniques.

The electronic device may be further operable to produce an output signal indicative of the determined at least one instantaneous operating condition of the component.

The method may comprise the further step of using the electronic device to produce an output signal indicative of the determined at least one instantaneous operating condition of the component.

The electronic device may be operable to produce an output signal indicative of one or more of the determined instantaneous operating conditions in the group consisting of: initial movement, contact of the component with a surface, slipping or sliding of the component with a surface, acceleration, deceleration, average speed, instantaneous speed, amount of extension, amount of flexion, and force applied by the component to a surface.

The electronic device may, in addition to being operable to produce an output signal indicative of one or more determined instantaneous operating conditions of the component, be operable to produce an output signal indicative of one or more historic operating conditions of the component. That is, the electronic device may be operable to produce an output signal indicative one or more historical actions performed by the component. From a knowledge of the instantaneous operating condition of the component and a knowledge of the historical operating conditions of the component the electronic device may be further operable to produce an output signal indicative of a change in any of the conditions, an average of any of the conditions, a forecasted or requested operating condition.

The electronic device may be operable to produce an output signal indicative of the relative position of the component. The relative position of the component may be one dimensional, two dimensional or three dimensional. The electronic device may be operable to produce an output signal indicative of the angle of the component, or a part thereof, to a reference plane, axis or point. The electronic device may be operable to produce an output signal indicative of the distance between at least two components, such as a finger and thumb.

The electronic device may be operable to produce an output signal indicative of conditions derived from any of the above-referenced conditions, such as a change in any of the conditions, or an average of any of the conditions.

The electronic device may be operable to produce an output signal indicative of one or more previous operating conditions, one or more forecasted and/or requested operating conditions.

The electronic device may be operable to produce an output signal indicative of a combination of any of the group consisting of: initial movement, contact of the component with a surface, slipping or sliding of the component with a surface, acceleration, deceleration, average speed, instantaneous speed, amount of extension, amount of flexion, and force applied by the component to a surface.

The electronic device may be further operable to produce an output signal indicative of a plurality of determined instantaneous operating conditions of the component.

The method may comprise the further step of using the electronic device to produce an output signal indicative of a plurality of determined instantaneous operating condition of the component.

The output signal may be indicative of a general operating condition of the component. The general operating condition of the component may include one or more modes of operation and/or configurations.

The method may comprise the further step of using the electronic device to produce an output signal indicative of a general operating condition of the component.

The electronic device may be further operable to produce an output signal which is indicative of a requested operating condition of the component from the wearer of the prosthesis or orthosis. The electronic device may be further operable to produce an output signal which is indicative of a completed operating condition of the component from the wearer of the prosthesis or orthosis.

The method may comprise the further step of using the electronic device to produce an output signal indicative of a requested operating condition of the component. The method may comprise the further step of using the electronic device to produce an output signal indicative of a completed operating condition of the component.

The electronic device may be further operable to use the output signal together with the operating parameters of the motor in a control strategy for the operation of the component. The electronic device may be further operable to use the output signal together with the operating parameters of the motor to control the operation of the component. For example, the output signal may indicate the relative position of the component and the electronic device may modify the operating parameter of the motor based on the output signal to achieve a requested position of the component, or the output signal may indicate the force exerted by the component on an object and the electronic device may modify the operating parameter of the motor based on the output signal to achieve a requested force from the component.

The method may comprise the further step of using the electronic device to use the output signal together with the operating parameters of the motor in a control strategy for the operation of the component.

Additionally, or alternatively, the electronic device may be further operable to communicate the output signal to the wearer of the prosthesis or orthosis.

The method may comprise the further step of using the electronic device to communicate the output signal to the wearer of the prosthesis or orthosis.

The output signal may be communicated to the wearer of the prosthesis or orthosis visually, kinaesthetically, aurally or neurally.

The output signal may be communicated to the wearer of the prosthesis or orthosis in one or more combinations of the above forms of communication.

The output signal is thus fed back to the wearer of the prosthesis or orthosis. The mode of feedback to the wearer of the prosthesis or orthosis may include vibrotactile or electrotactile.

The output signal may be fed back to the wearer of the prosthesis or orthosis at a stump, arm or healthy hand, shoulder, neck, foot, tongue, or the like.

In this arrangement the wearer of the prosthesis or orthosis receives a signal from the electronic device which indicates to them an instantaneous operating condition of the component. Thus, for example, the wearer of the prosthesis or orthosis receives a feedback signal from the prosthesis or orthosis which indicates the current force being applied by the component to a surface or object. The wearer therefore knows if the current force being applied to the surface or object is suitable for their needs, or if a greater or lesser force is required. For example, if the wearer is trying to push a button with the component of the prosthesis, they will receive a feedback signal which indicates to them if the component is pressing against the button with sufficient force to allow the button to be depressed. Also, if the wearer is trying to move an object with the component of the prosthesis, they may receive a feedback signal which indicates to them if the component is pushing, pulling, squeezing or lifting the object with sufficient force to allow the object to be moved.

This is just one example of the information which may be fed back to the wearer. It should be appreciated that the output signal fed back to the wearer of the prosthesis or orthosis may include more than one instantaneous operating condition of the component.

The prosthesis or orthosis may comprise a plurality of moveable components, with each component having a motor and electronic device.

Alternatively, the prosthesis or orthosis may comprise a plurality of moveable components, with each motor having a motor, but only a single electronic device. In this arrangement the electronic device may be operable to determine the instantaneous operating parameters of each motor, map the instantaneous operating parameter of each motor to a predetermined operating profile of each motor and component, and determine the instantaneous operating condition of each component from the predetermined operating profile of each motor and component.

The method may comprise the further step of using the electronic device to determine the instantaneous operating parameters of each motor, map the instantaneous operating parameter of each motor to a predetermined operating profile of each motor and component, and determine the instantaneous operating condition of each component from the predetermined operating profile of each motor and component.

The prosthesis or orthosis may comprise one or more first components acting as fingers and second component acting as a thumb. In this arrangement the electronic device may be further operable to determine the grasp aperture between the fingers and thumb and undesired movement between the component and an object, i.e. a slip condition, between the fingers and thumb when each component is bearing against a surface or object. The grasp aperture and slip condition here being examples of operating conditions of the components.

BRIEF DESCRIPTION OF THE DRAWINGS

Embodiments of the present invention will now be described by way of example only with reference to the following drawing, of which.

DETAILED DESCRIPTION OF THE DRAWINGS

Figure 1:
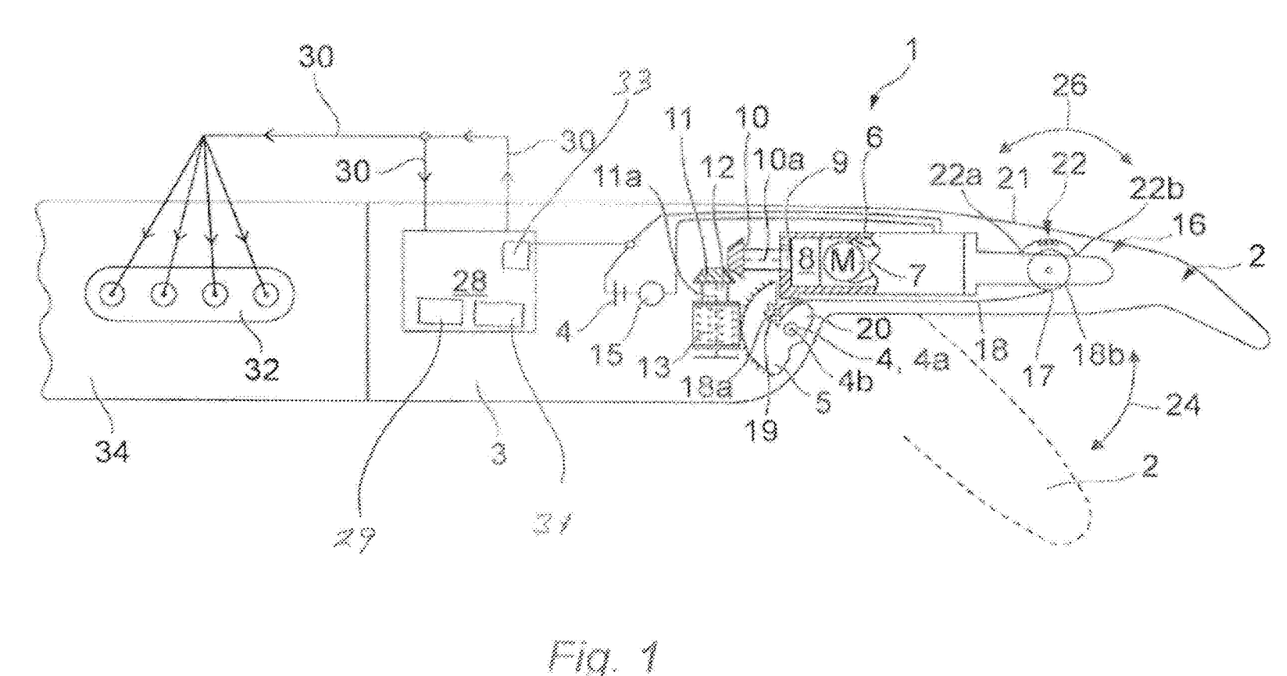
FIG. 1 is a partly cut-away view of a digit member of a prosthesis according to the present invention.

FIG. 1 illustrates a partly cut-away view of a hand prosthesis 1 having a finger 2 (an example of a moveable component or digit). The prosthesis 1 is securely fixed in use to a wearer's hand stump (see below) in a generally known manner by means of a socket component body (not shown). The prosthesis 1 has a main body 3 which has a spindle 4 on which a gear wheel 5 is fixedly mounted. The gear wheel 5 is of roughly semi-circular profile. The finger 2 extends generally tangentially with respect to the gear wheel 5. The finger 2 has a generally tubular housing 6, in which is mounted a motor 7 having a gearbox system 8. The gearbox system 8 provides for different torque output drive speed ratios to be selected from a range of different ratios. Lugs (not shown) depend from the underside of the tubular housing 6 and are rotatably mounted to the spindle 4 to allow for rotation of the finger 2 in relation to the spindle 4 and gear wheel 5. The spindle 4 has a centre 4a which defines an axis 4b about which the finger 2 rotates. The housing 6 containing the motor 7 corresponds to the proximal phalanx of a finger and the joint formed between the spindle 4 and the lugs depending from the housing 6 correspond to the metacarpophalangeal (MCP) or knuckle joint of a finger.

A drive shaft 9 extends from the motor 7 and gearbox system 8. A first bevel gear 10 is mounted on the distal end of the drive shaft 9. A second bevel gear 11 is mounted within the prosthesis 1 such that an axis of rotation 11a of the second bevel gear 11 is at substantially 90 degrees to an axis of rotation 10a of the first bevel gear 10.

The gear ratio of the first and second bevel gears 10, 11 is substantially 1:1, although the gear ratio can be readily changed by known means. The second bevel gear 11 is mounted on a shaft 12, which also includes a worm 13. The worm 13 is located such that it engages with a toothed, curved peripheral edge of the gear wheel 5. As illustrated in FIG. 1, the worm 13 extends laterally to the housing 6 at an angle of substantially 90 degrees. The worm 13 and the gear wheel 5 have a 25:1 reduction ratio.

In the embodiment illustrated here the worm 13 is located in the prosthesis 1 such that it is outside the housing 6. Thus the worm 13 is located within the main body 3 of the prosthesis 1 and not the finger 2, even though the prosthesis 1 is structured such that the worm 13 moves with the housing 6 upon operation of the finger 2, as described below. However, it should also be appreciated that in other embodiments of the prosthesis the worm 13 may be located in the housing 6.

In the embodiment illustrated and described here the motor 7 is a permanent magnet DC motor having a substantially linear relationship between torque and drive current. In normal use the motor rotates at around 21,000 rpm. The motor is powered by small rechargeable batteries 14, which may be mounted remotely of the prosthesis 1.

The motor 7 is operable to move the finger 2, as described in more detail below. The motor 7 operates by application of an appropriate electrical signal, i.e. a current/voltage signal (an example of at least one operating parameter of the motor).

The motor 7 is controlled by means of switches 15, which are actuated by known means, e.g. residual digit movement or wrist/shoulder movement of the wearer of the prosthesis 1. Alternatively, or in addition, control may be via signals derived from electromyographic (EMG) activity of residual muscle actions of the wearer of the prosthesis 1, or pressure sensitive resistors on the wearer of the prosthesis 1, or signals derived from one or more neural implants in the wearer of the prosthesis 1, or EMG activity from reinnervated muscles, muscles of the feet and/or chest, or the like.

In forms of the invention in which the prosthesis 1 comprises a plurality of other digits, i.e. a thumb and one or more other fingers (FIG. 2), control by known means may provide for independence of movement of the digits or groups of digits. In the case of a finger or a thumb the motor 7 has low speed, high torque characteristics.

The finger 2 has a finger tip portion 16 corresponding to the middle and distal phalanges of a finger, which forms with the distal end of the housing 6 a proximal joint 17 corresponding to a proximal intermediate phalangeal (PIP) joint of a finger. Arrow 24 represents movement of the finger 2 about axis 4b (i.e. the MCP joint) and arrow 26 represents movement of finger tip portion 16 about PIP joint 17. An inextensible belt or chord 18 is attached at a first end 18a to the gear wheel 5 in an aperture 19 provided in the gear wheel 5. The belt or chord 18 passes over a protrusion 20 formed on the gear wheel 5 and attaches at a second end 18b to the finger tip portion 16. A helical spring 22 is connected at one end 22a to the end of housing 6 and at a second opposing end 22b to the finger tip portion 16. The prosthesis is clad in a known manner with an overlay 21 of silicone rubber or the like to provide an aesthetically acceptable appearance which is as similar as practicable to a normal hand.

The prosthesis 1 further comprises an electronic device 28 containing electronic circuitry, which is operable to control the operation of the motor 7. That is, the electronic device 28 is operable to apply the current/voltage signals to the motor 7 to control the operation thereof. The electronic device 28 comprises an H-bridge, or the like, which is used to provide bi-directional drive of the motor 7.

The electronic device 28 includes a digital signal controller device 29 and a memory device 31. The control processes of the prosthesis 1 performed by the electronic device 28 are embodied in firmware, which is stored in and executed on the digital signal controller device 29 and the memory device 31.

The electronic device 28 also comprises a current measurement circuit 33, which is configured to measure current drawn through the H-bridge and, therefore, motor 7. It should be appreciated that the electronic device 28 may additionally, or alternatively, comprise a voltage measurement circuit, which is configured to measure the voltage drop across the H-bridge and, therefore, motor 7.

Therefore, in addition to the electronic device 28 being operable to control the drive of the motor 7, it is also operable to determine the current/voltage signal applied to the motor 7. The electronic device 28 is operable to determine the current/voltage signal applied to the motor 7 at any given time. Thus, the electronic device 28 is therefore operable to determine the instantaneous current/voltage signal applied to the motor 7.

In use, the wearer of the prosthesis 1 actuates the finger 2 by one of the means described above, e.g. by way of EMG activity of residual muscle actions. Operation of the motor 7 in response to actuation causes rotation of the first bevel gear 10, which rotates the second bevel gear 11 together with the worm 13. As the worm 13 rotates it progresses around the peripheral surface of the fixed gear wheel 5 either clockwise or anti-clockwise depending on the direction of rotation of the motor 7. This moves the finger 2 about the axis 4b in the direction indicated by arrow 24. As the finger 2 moves about axis 4b in a downward direction the distance between the point of attachment of the belt 18 in aperture 19 of the worm gear wheel 5 and the proximal joint 17 reduces. This is because the aperture 19 is offset from the axis 4b of the gear wheel 5 as shown in FIG. 1.

As the distance reduces the fixed length belt 18 pulls the finger tip portion 16 against the bias of the helical spring 22 to rotate the finger tip portion 16 clockwise in relation to the rest of the finger 2. Upon reversal of the direction of rotation of the finger 2 about the axis, i.e. movement of the finger 2 upwards, tension is released on the belt 18 and the spring 22 exerts a bias on the finger tip portion 16 to return the finger tip portion 16 to the extended position illustrated in FIG. 1.

The movement of the finger 2 as a result of the above-described operation of the motor 7 is an example of the finger 2 having at least one operating condition. However, operating conditions of the finger 2 may also include: initial movement, contact of the finger 2 with a surface, slipping or sliding of the finger 2 with a surface, acceleration, deceleration, average speed, instantaneous speed, amount of extension, amount of flexion, and force applied by the finger 2 to a surface. It should also be appreciated that the operating condition of the finger 2 may include any combination of the group consisting of: initial movement, contact of the finger 2 with a surface, slipping or sliding of the finger 2 with a surface, acceleration, deceleration, average speed, instantaneous speed, amount of extension, amount of flexion, and force applied by the finger 2 to a surface. It should also be appreciated that the operating condition of the finger 2 may include a plurality of any of the group consisting of: initial movement, contact of the finger 2 with a surface, slipping or sliding of the finger 2 with a surface, acceleration, deceleration, average speed, instantaneous speed, amount of extension, amount of flexion, and force applied by the finger 2 to a surface.

Furthermore, the operating condition of the finger 2 may also include a general operating condition of the finger 2, e.g. "on/off", or a mode of operation and/or configuration of the finger 2. The mode of operation and/or configuration of the finger 2 may include different types of grasps, such as a "power" grasp or a "precision" grasp. These different modes of operation have different operating characteristics.

The relationship between the instantaneous current/voltage signal applied to the motor 7 and the current/voltage drawn by or dropped across the motor 7 (i.e. motor load) is a complex function of, inter alia, the current/voltage signal applied to the motor 7, the hardness of the surface or object which the finger 2 impinges upon, finger movements and mechanical leverage, nonlinearities and variability in fabrication of gearing, location of contact/load on finger 2.

The memory device of the electronic device 28 has stored thereupon a predetermined operating profile of the motor 7 and finger 2. The operating profile of the motor 7 and finger 2 is based on one or more operating parameters inputs to the motor 7 and one or more operating condition outputs of the finger 2. That is, the operating profile of the motor 7 and finger 2 is based on one or more current/voltage inputs to the motor 7 and one or more operating condition outputs of the finger 2, such as one of those referenced above.

The operating profile of the motor 7 and finger 2 includes a plurality of data sets representative of a plurality of operating parameter inputs to the motor 7 and a plurality of resulting operating condition outputs of the finger 2. The operating profile of the motor 7 and finger 2 is obtained by characterising the operation of the finger 2 as a function of current/voltage input to the motor 7. The operating profile of the motor 7 and finger 2 also includes a plurality of data sets representative of the instantaneous current/voltage inputs to the motor 7 as a function of the instantaneous operating condition of the finger 2.

The operating profile of the motor 7 and finger 2 also includes a plurality of data sets representative of at least one of the following operating conditions of the finger 2: initial movement, contact of the finger 2 with a surface, slipping or sliding of the finger 2 with a surface, acceleration, deceleration, average speed, instantaneous speed, amount of extension, amount of flexion, and force applied by the finger 2 to a surface; and corresponding current/voltage inputs to the motor 7.

The operating profile of the motor 7 and finger 2 is, for example, obtained by characterising the operation of the motor 7 as a function of one or more operating conditions of the finger 2. The finger 2 is instructed by the wearer, or an external control program, to perform one or more of the above-listed operating actions (conditions) and the resulting current/voltage operating parameters of the motor 7 are measured. The current drawn by the motor 7 and/or the voltage drop across the motor 7 is determined as the finger 2 carries out its instructed task. This characterising of the motor 7 and finger 2 is carried out over a plurality of operating conditions of the finger 2.

The operating profile of the motor 7 and finger 2 is determined by a mathematical model based on the above-described motor inputs and finger outputs. The mathematical model may be a mathematical function, numerical mapping, or the like. The mathematical model may be a neural network, an artificial neural network, decision tree (DT), support vector Machine (SVM), logistic regression (LR), other such "machine learning" techniques.

The electronic device 28 is further operable to determine at least one instantaneous operating condition of the finger 2 from the predetermined operating profile of the motor 7 and finger 2 stored on the memory device and the determined current/voltage operating parameters of the motor 7. That is, the electronic device 28 is capable of determining from a measurement of the current/voltage parameter of the motor 7 the instantaneous operating condition of the finger 2.

The electronic device 28 does this by firstly measuring the current/voltage drawn by, or dropped across, the motor 7; then mapping, or comparing, the measured current voltage to the predetermined operating profile of the motor 7 and finger 2 stored on the memory device. From the operating profile of the motor 7 and finger 2 the electronic device 28 is able to determine the instantaneous operating condition of the finger 2. For any given operating condition of the finger 2, such as those recited above, the motor 7 has a current/voltage "signature". The electronic device 28 determines the current/voltage signature of the motor 7 and then uses the operating profile to determine the operating condition of the finger 2 to which it relates.

The electronic device 28 includes firmware which is operable to perform the mapping of the measured current voltage to the predetermined operating profile of the motor 7 and finger 2.

The electronic device 28 may measure the instantaneous current/voltage operating parameter of the motor 7 or the electronic device 28 may, for example, take an average current/voltage measurement of the motor 7. The electronic device 28 is required to be operable such that it is capable of determining the current/voltage "signatures" of the motor.

The electronic device 28 is also operable to determine an historic operating condition of the finger 2. That is, the electronic device 28 is capable of accessing historical information regarding the operation of the finger 2. This information may, for example, be stored on the memory device. From a knowledge of the instantaneous operating condition of the finger 2 and a knowledge of the historical operating conditions of the finger 2 the electronic device 28 is further operable to determine a change in any of the conditions of the finger 2, an average of any of the conditions of the finger 2, a forecasted or requested operating condition of the finger 2.

The electronic device 28 is further operable to produce an output signal which is indicative of the instantaneous operating condition of the finger 2. Furthermore, the electronic device 28 is also operable to produce an output signal which is indicative of an historic operating condition of the finger 2. This is a result of the electronic device 28 being capable of determining both the instantaneous operating condition of the finger 2 and the historic operating condition of the finger 2. The output signal 30 may represent any of the operating conditions of the finger 2 described above, including changes, averages, previous conditions, forecasted conditions or 25 requested conditions.

The electronic device 28 is also operable to use the output signal 30 together with the current/voltage operating parameters of the motor 7 in a control strategy for the operation of the finger 2. In this arrangement the electronic device 28 uses the output signal 30 together with the current/voltage operating parameters of the motor 7 to control the operation of the motor 7. In this arrangement the output signal 30 is fed back to the electronic device 28 as in input thereto. The output signal 30 may, for example, indicate the relative position of the finger 2 and the electronic device 28 may modify the current/voltage operating parameters of the motor 7 based on the output signal 30 to achieve a requested position of the finger 2, or to correct for any error in a requested position of the finger 2. As a further example, the output signal 30 may indicate the force exerted by the finger 2 on an object and the electronic device 28 may modify the current/voltage operating parameters of the motor 7 based on the output signal 30 to achieve a requested force from the finger 2. Thus the output signal 30 may function with the electronic device 28 in a feedback control loop arrangement to modify the operation of the finger 2.

The above arrangement provides proportional linear control of the operation of the finger 2. That is, the wearer of the prosthesis 1 knows that there is a linear relationship between the EMG signal that they apply to the prosthesis 1 and, for example, the force applied by the finger 2 to an object or surface. This operation of the finger 2 is extremely advantageous to the wearer of the prosthesis 1. For example, this provides the wearer of the prosthesis 1 with increased confidence when handling delicate objects, particularly so when the prosthesis 1 includes a plurality of fingers 2 and a thumb component (see below).

Additionally, or alternatively, the electronic device 28 is operable to communicate the output signal 30 to the wearer of the prosthesis 1. That is, the electronic device 28 is operable to feedback an operating condition of the finger 2. Thus the wearer of the prosthesis 1 is able to receive operating information about the finger 2. For example, the wearer of the prosthesis 1 is able to know the force that the finger 2 is applying to an object.

The output signal 30 may be communicated to the wearer of the prosthesis 1 by, for example, any of the following means: visually, kinaesthetically, aurally or neurally.

Figure 2:
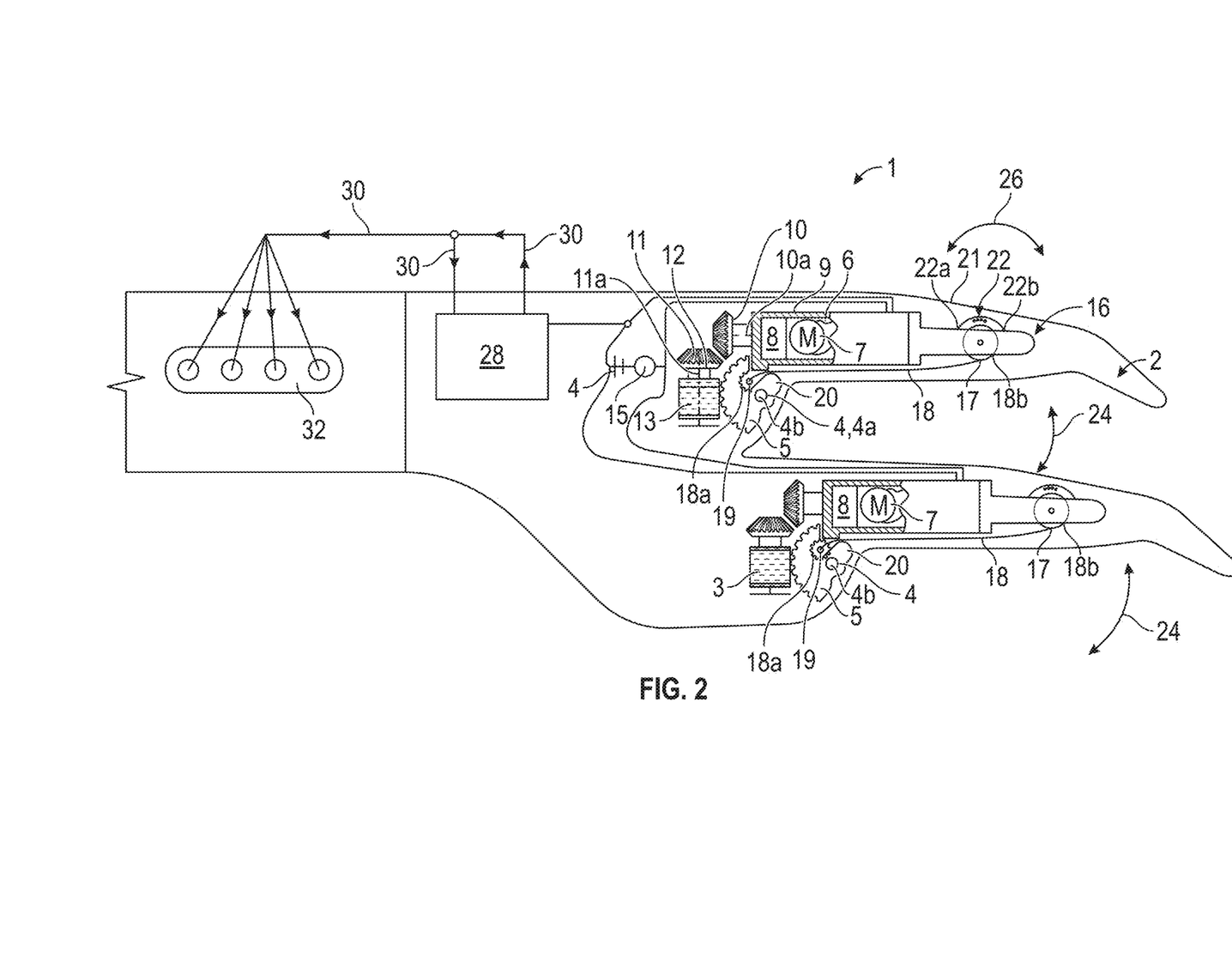
FIG. 2 is a diagram with two embodiments of the digit of FIG. 1 incorporated into two digits of a hand prosthesis.

In one arrangement the mode of feedback to the wearer of the prosthesis 1 may be vibrotactile. In this arrangement the wearer of the prosthesis 1 has a number of vibrotactors 32 (vibrating motors) mounted to, for example, their forearm 34 (stump). The output signal 30 is decoded (by, for example, the electronic device 28) to produce an operating mode for the vibrotactors 32. The operating mode for the vibrotactors 32 indicates to the wearer of the prosthesis 1 the operating condition of the finger 2. Due to the large number of operating conditions of the finger 2, there are clearly a large number of operating modes for the vibrotactors 32. Conditions of operation of the vibrotactors 32 may include amplitude, frequency, pulse width, period, number of pulses, period between pulses, patterns of operation between vibrotactors 32 etc. The wearer of the prosthesis 1 learns to recognise the modes of operation of the vibrotactors 32 and operating condition of the finger 2 by, for example, performing a number of tasks with the finger 2.

In one operating example the wearer of the prosthesis 1 receives a feedback signal from the prosthesis 1 which indicates the current force being applied by the finger 2 to a surface or object. The wearer therefore knows if the force being applied to the surface or object is suitable for their needs, or if a greater or lesser force is required. For example, if the wearer is trying to push a button with the finger 2 of the prosthesis 1, they will receive a feedback signal which indicates to them if the component is pressing against the button with sufficient force to allow the button to be depressed. Also, if the wearer is trying to move an object with the finger 2 of the prosthesis 1, they may receive a feedback signal which indicates to them if the component is pushing, pulling, squeezing or lifting the object with sufficient force to allow the object to be moved.

The above arrangement again provides proportional linear control of the operation of the finger 2 in the same manner as described above.

It should be appreciated that the output signal 30 fed back to the wearer of the prosthesis 1 may be indicative of a plurality of instantaneous operating conditions of the finger 2.

Although the prosthesis has been illustrated and described above as comprising a single finger 2, it should be appreciated that the prosthesis 1 may comprise a plurality of moveable fingers 2, with each finger 2 including a motor 7 and an electronic device 28, such that each finger 2 operates in the same manner described above. Alternatively, the prosthesis 1 may comprise a plurality of fingers 2, with each finger 2 having a motor 7, but only a single electronic device 28. In this arrangement the electronic device 28 is operable to determine the instantaneous operating parameters of each motor 7, map the instantaneous operating parameter of each motor 7 to a predetermined operating profile of each motor 7 and finger 2, and determine the instantaneous operating condition of each finger 2 from the predetermined operating profile of each motor 7 and finger 2.

The prosthesis 1 may comprise one or more moveable components 2 acting as fingers and a second component 2 acting as a thumb. In this arrangement the electronic device 28 is further operable to determine the grasp aperture between the fingers and thumb and undesired movement between the components 2 and an object, i.e. a slip condition, between the fingers and thumb when each component 2 is bearing against a surface or object. The grasp aperture and slip condition here being examples of operating conditions of the components 2.

Figure 3:
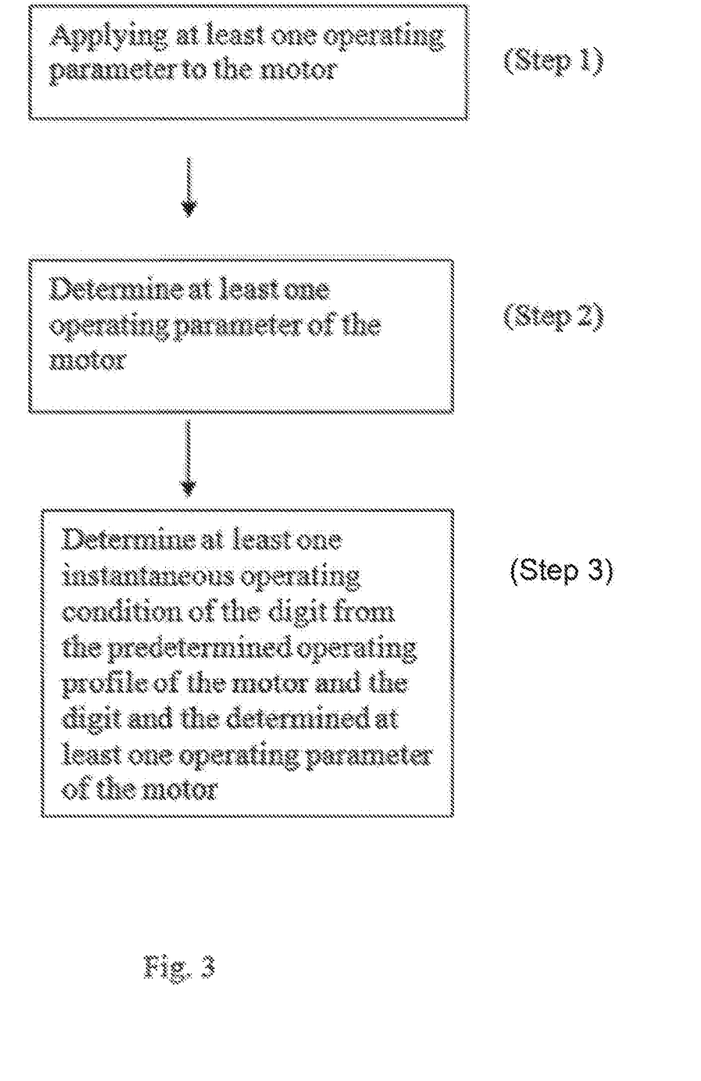
FIG. 3 is a flow diagram of an embodiment of the method of the invention.

In summary, the invention provides a method of operating a prosthesis or orthosis having a moveable digit, a motor operable to move the digit and an electronic device to control the movement of the digit. The motor has at least one operating parameter, the application of which to the motor results in the digit having at least one operating condition. In one embodiment, and referring to FIG. 3, the method comprises the steps of: applying at least one operating parameter to the motor (Step 1) and using the electronic device to determine at least one operating parameter of the motor (Step 2). The electronic device then determines (Step 3) at least one instantaneous operating condition of the digit from the predetermined operating profile of the motor and the digit and the determined at least one operating parameter of the motor, the predetermined operating profile of the motor and the digit being based on one or more operating parameter inputs to the motor and one or more resulting operating condition outputs of the digit.

Modifications and improvements may be made to the above without departing from the scope of the invention, for example, although the electronic device 28 has been described above as determining (measuring) the instantaneous operating parameter (current/voltage) of the motor 7, it should be appreciated that the electronic device 28 may be configured to determine (measure), or sample, the current/voltage operating parameters of the motor 7 over a period of time and, for example, take an average measurement.

Furthermore, although the above embodiment has been described with reference to a finger component of a hand prosthesis, it should be appreciated that the present invention is also applicable to moveable components on other forms of prosthesis, such as toes of a foot prosthesis, of moveable components of an orthosis. It should also be appreciated that the present invention is also applicable to any components which link, or interconnect, between moveable components of a prosthesis or orthosis.

What is claimed is:
1. A system for controlling an upper-limb prosthesis, comprising:
 a controller communicatively coupled to a first motor and a second motor, the controller configured to:

communicate first and second control signals to the first and second motors, respectively, the first motor configured to manipulate a thumb digit of the upper-limb prosthesis based at least in part on the first control signal, the second motor configured to manipulate a finger digit of the upper-limb prosthesis based at least in part on the second control signal;

determine a first current drawn from a power source by the first motor to manipulate the thumb digit, determine a second current drawn from the power source by the second motor to manipulate the finger digit;

identify a slip condition corresponding to at least one of the thumb digit or the finger digit, wherein to identify the slip condition, the controller is configured to:

compare the first current with one or more first data sets to identify an operating condition of the thumb digit, wherein the one or more first data sets associates different first current values with different operating conditions of the thumb digit including the identified operating condition of the thumb digit, compare the second current with one or more second data sets to identify an operating condition of the finger digit, wherein the one or more second data sets associates different second current values with different operating conditions of the finger digit including the identified operating condition of the finger digit, and determine the slip condition based at least in part on at least one of the identified operating condition of the thumb digit or the identified operating condition of the finger digit; and output an indication of the slip condition.

2. The system of claim 1, wherein the slip condition indicates that at least one of the thumb digit or the finger digit is at least one of slipping or sliding with respect to a surface of an object gripped between the thumb digit and the finger digit.

3. The system of claim 1, wherein actuation of the first motor results in the first motor drawing the first current from the power source and actuation of the second motor results in the second motor drawing the second current from the power source.

4. The system of claim 1, wherein the first control signal causes the thumb digit to initiate at least a portion of a pinch grip and the second control signal causes the finger digit to initiate at least a portion of the pinch grip.

5. The system of claim 1, wherein the indication of the slip condition comprises vibrotactile feedback.

6. The system of claim 1, wherein the finger digit is a first finger digit, the controller is further communicatively coupled to a third motor, and the controller is further configured to:

communicate a third control signal to the third motor, the third motor configured to manipulate a second finger digit of the upper-limb prosthesis based at least in part on the third control signal;

determine a third current drawn from the power source by the third motor to manipulate the second finger digit; and compare the third current with one or more third data sets to identify an operating condition of the second finger digit, wherein the one or more third data sets associates different third current values with different operating conditions of the second finger digit;

wherein the slip condition further corresponds to the second finger digit, wherein identification of the slip condition is further based at least in part on the operating condition of the second finger digit.

7. The system of claim 1, wherein at least one of the first motor or the second motor is a worm gear motor.

8. The system of claim 1, wherein at least one of the first motor or the second motor is a stepper motor.

9. The system of claim 1, wherein at least one of the first control signal or the second control signal is based on electromyographic activity of a wearer of the upper-limb prosthesis.

10. The system of claim 1, wherein the slip condition corresponds to at least one of a change in the first current over a period of time or a change in the second current over the period of time.

11. The system of claim 10, wherein the slip condition corresponds to at least one of a reduction in the first current over the period of time or a reduction in the second current over the period of time.

12. The system of claim 1, wherein the slip condition indicates at least one of the thumb digit or the finger digit is moving after transitioning from a resting position.

13. An apparatus for controlling an upper-limb prosthesis, comprising:

a controller communicatively coupled to a first motor and a second motor, the controller configured to:

communicate first and second control signals to the first and second motors, respectively, the first motor configured to manipulate a thumb digit of the upper-limb prosthesis based at least in part on the first control signal, the second motor configured to manipulate a finger digit of the upper-limb prosthesis based at least in part on the second control signal;

determine a first current drawn from a power source by the first motor to manipulate the thumb digit, determine a second current drawn from the power source by the second motor to manipulate the finger digit;

identify a slip condition corresponding to at least one of the thumb digit or the finger digit, wherein to identify the slip condition, the controller is configured to:

compare the first current with one or more first data sets to identify an operating condition of the thumb digit, wherein the one or more first data sets associates different first current values with different operating conditions of the thumb digit including the identified operating condition of the thumb digit, compare the second current with one or more second data sets to identify an operating condition of the finger digit, wherein the one or more second data sets associates different second current values with different operating conditions of the finger digit including the identified operating condition of the finger digit, and determine the slip condition based at least in part on at least one of the identified operating condition of the thumb digit or the identified operating condition of the finger digit; and output an indication of the slip condition.

14. The apparatus of claim 13, wherein the slip condition indicates that at least one of the thumb digit or the finger digit is at least one of slipping or sliding with respect to a surface of an object gripped between the thumb digit and the finger digit.

15. The apparatus of claim 13, wherein actuation of the first motor results in the first motor drawing the first current from the power source and actuation of the second motor results in the second motor drawing the second current from the power source.

16. The apparatus of claim 13, wherein the first control signal causes the thumb digit to initiate at least a portion of a pinch grip and the second control signal causes the finger digit to initiate at least a portion of the pinch grip.

17. The apparatus of claim 13, wherein the finger digit is a first finger digit, wherein the controller is further communicatively coupled to a third motor, and wherein the controller is further configured to:
  communicate a third control signal to the third motor, the third motor configured to manipulate a second finger digit of the upper-limb prosthesis based at least in part on the third control signal;
  determine a third current drawn from the power source by the third motor to manipulate the second finger digit; and
  compare the third current with one or more third data sets to identify an operating condition of the second finger digit, wherein the one or more third data sets associates different third current values with different operating conditions of the second finger digit;
  wherein the slip condition further corresponds to the second finger digit,
  wherein identification of the slip condition is further based at least in part on the operating condition of the second finger digit.

18. The apparatus of claim 13, wherein the slip condition corresponds to at least one of a change in the first current over a period of time or a change in the second current over the period of time.

19. The apparatus of claim 13, wherein the slip condition corresponds to at least one of a reduction in the first current over the period of time or a reduction in the second current over the period of time.

20. The apparatus of claim 13, wherein the slip condition indicates at least one of the thumb digit or the finger digit is moving after transitioning from a resting position.

* * * * *